(12) United States Patent
Li

(10) Patent No.: US 11,008,581 B2
(45) Date of Patent: May 18, 2021

(54) METHOD OF PRODUCING NOVEL ROOTSTOCK PLANTS HAVING IMPROVED GRAFTING TRAITS

(71) Applicant: University of Connecticut, Farmington, CT (US)

(72) Inventor: Yi Li, Storrs, CT (US)

(73) Assignee: University of Connecticut, Farmington, CT (US)

(*) Notice: Subject to any disclaimer, the term of this patent is extended or adjusted under 35 U.S.C. 154(b) by 192 days.

(21) Appl. No.: 15/985,293

(22) Filed: May 21, 2018

(65) Prior Publication Data

US 2018/0334680 A1 Nov. 22, 2018

Related U.S. Application Data

(60) Provisional application No. 62/508,661, filed on May 19, 2017.

(51) Int. Cl.
C12N 15/82 (2006.01)

(52) U.S. Cl.
CPC ..... *C12N 15/8243* (2013.01); *C12N 15/8227* (2013.01); *C12N 15/8294* (2013.01); *C12N 15/8295* (2013.01)

(58) Field of Classification Search
None
See application file for complete search history.

(56) References Cited

U.S. PATENT DOCUMENTS

2012/0185975 A1* 7/2012 Chiou .................. C12N 9/1051
800/317.3

OTHER PUBLICATIONS

Albburquerque et al. (Pest Manag sci., 73:2163-2173, 2017).*
Yin et al. (Mol. Plant Microbe Interact., 27:227-235, 2014).*
Sitborn et al. (Plant Physiol., 99:1062-1069, 1992).*
Doerks et al., (TIG, 14:248-250, 1998).*
Melnyk et al. (Curr. Biol., 25 (5):R183-R188, 2015).*
Smith et al. (Nature Biotechnology, 15:1222-1223, 1997).*
Bork et al. (TIG, 12:425-427, 1996).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Wang et al. (Sci. Bull. 60(6):616-628, 2015).*
Barker et al. (GenBank sequence Accession No. AF242881.1; Published Dec. 22, 2006).*
Arshad et al., "Agrobacterium-Mediated Transformation of Tomato with rolB Gene Results in Enhancement of Fruit Quality and Foliar Resistance against Fungal Pathogens," PLos One, 9, e96979 (2014).

Artlip et al., "An apple rootstock overexpressing a peach CBF gene alters growth and flowering in the scion but does not impact cold hardiness or dormancy," Horticulture Research, 3, 16006 (2016).
Bellini et al., "Adventitious roots and lateral roots: similarities and differences," Annual review of plant biology, 65, 639-666 (2014).
Cary et al., "Cytokinin action is coupled to ethylene in its effects on the inhibition of root and hypocotyl elongation in *Arabidopsis thaliana* seedlings," Plant Physiol. 107, 1075-1082 (1995).
Chen et al., "In vitro regeneration and Agrobacterium-mediated genetic transformation of Euonymus alatus," Plant Cell Rep, 25:1043-1051D01 10.1007/s00299-006-0168-8 (2006).
Chiou et al., "Characterization of the Scutellaria barbata glycosyltransferase gene and its promoter," Planta, 232:963-974 plus 6 pages of Supplementary Marterials, DOI 10.1007/s00425-010-1229-3 (2010).
Choi et al., "Using chemical controls to inhibited axillary buds of Lagemaria as rootstock for grafted watermelon (*Cilrullus lanalus*)," Acta hort. 588, 43-48 (2002).
Cousins, "Rootstock breeding: An analysis of intractability," Hor/science, 40,1945-1946 (2005).
Daley et al., "Fatty alcohol application to control meristematic regrowth in bottle gourd and interspecific hybrid squash rootstocks used for grafting watermelon" Hortscience, 49, 260-264 (2014).
Eliasson et al., "Inhibitory action of auxin on root elongation not mediated by ethylene," Plant Physiol, 91, 310-314 (1989).
Ferguson et al., "Roles for Auxin, Cytokinin, and Strigolactone in Regulating Shoot Branching," Plant Physiol, 149, 1929-1944 (2009).
Gambino et al., "Genetic transformation of fruit trees: current status and remaining challenges," Transgenic Res. 21, 1163-1181 (2012).
Gao et al., "Cytokinin Oxidase/Dehydrogenase4 Integrates Cytokinin and Auxin Signaling to Control Rice Crown Root Formation," Plant Physiol, vol. 165, pp. 1035-1046,16 (Jul. 2014).
Goldschmidt, "Plant grafting: new mechanisms, evolutionary implications," Frontiers in Plant Science, 5, 1-9 (2014).
Zheng et al., "The cauliflower mosaic virus (CaMV) 35S promoter sequence alters the level and panems of activity of adjacent tissue- and organ-specific gene promoters," Plant Cell Rep. 26, 1195-1203 (2007).
Guilfoyle et al., "Auxin-regulation transcription," Austral J. Plant Physiology, 20: 489-506 (1993).
Zhu et al., "The rooting ability of the dwarfing pear rootstock BP10030 (*Pyrus communis*) was significantly increased by introduction of the rolB gene," Plant Sci. 165, 829-835 (2003).
Jones et al., "Cytokinin regulation of auxin synthesis in *Arabidopsis* involves a homeostatic feedback loop regulated via auxin and cytokinin signal transduction," Plant Cell, 22, 2956-2969 (2010).
Kausch et al., "Transgenic perennial biofuel feedstocks and strategies for bioconfinement," Biofuels, 1, 163-176 (2010).
Krishnan et al., "Drought Stress and Trinexapac-ethyl Modify Phytohormone Content Within Kentucky Bluegrass Leaves," J Plant Growth Regul, 34, 1-12 (2015).

(Continued)

*Primary Examiner* — Vinod Kumar

(74) *Attorney, Agent, or Firm* — Michael Best & Friedrich LLP

(57) ABSTRACT

Disclosed are rootstock plants, and methods of producing the rootstock plants, characterized by improved grafting success, enhanced root growth and other performance parameters.

12 Claims, 10 Drawing Sheets

Specification includes a Sequence Listing.

(56) References Cited

OTHER PUBLICATIONS

Krishnan et al., "Leaf Trimming and High Temperature Regulation of Phytohormones and Polyamines in Creeping Bentgrass Leaves," J. Am. Soc. Hortic. Sci. 141, 66-75 (2016).
Laplaze et al., "Cytokinins act directly on lateral root founder cells to inhibit root initiation," Plant Cell, 19, 3889-3900 (2007).
Lee et al., "Grafting of herbaceous vegetable and ornamental crops," Horticultural Reviews, 28, 61-124 (2010).
Li et al., "Altered morphology in transgenic tobacco plants that overproduce cytokinins in specific tissues and organs," Dev. Biol., 153, 386-395 (1992).
Li et al., "The soybean SAUR open reading frame contains a cis element responsible for cycloheximide-induced mRNA accumulation," Plant Mo/. Biol. 24, 715-723 (1994).
Li et al., "Expression of the Auxin-Inducible GH3 Promoter/GUS Fusion Gene as a Useful Molecular Marker for Auxin Physiology," Plant Cell Physiol., 40, 675-682 (1999).
Li et al., "An AGAMOUS intron-driven cytotoxin leads to flowerless tobacco and produces no detrimental effects on vegetative growth of either tobacco or poplar," Plant Biotechnol. J. 14, 2276-2287 (2016).
Melnyk et al., "Plant grafting," Curr. Biol. 25, RI 83-R188 (2015).
Memmott et al., "Watermelon (*Citrullus lanatus*) grafting method to reduce labor cost by eliminating rootstock side shoots," In: IV International Symposium on Cucurbils 871 pp. 389-394 (2009).
Muller et al., "Auxin, cytokinin and the control of shoot branching," Ann. Bot. London, 107, 1203-1212 (2011).
Nakamura et al., "Conferring high-temperature tolerance to nontransgenic tomato scions using graft transmission of RNA silencing of the fatty acid desaturase gene," Plant Biotechnol. J. 14, 783-790 (2016).
Pawlicki et al., "Influence of carbohydrate source, auxin concentration and time of exposure on adventitious rooting of the apple rootstock Jork 9," Plant Sci. 106, 167-176 (1995).
Pinto, "Insights into rootstock biology under low oxygen," Chilean journal of agricultural research, 75, 3-5 (2015).
Porebski et al, "Modification of a CTAB DNA extraction protocol for plants containing high polysaccharide and polyphenol components," Plant Mol. Biol. Rep. 15, 8-15 (1997).
Riefler et al., "*Arabidopsis* cytokinin receptor mutants reveal functions in shoot growth, leaf senescence, seed size, germination, root development, and cytokinin metabolism," Plant Cell, 18, 40-54 (2006).
Park et al., "Stable internal reference genes for normalization of real-time RT-PCR in Different Sweetpotato Cultivars Subjected to Abiotic Stress Conditions," PLOS One, vol. 7, Issue 12, pp. 1-9 (2012) www.plosone.org.
Sitbon et al., "Transgenic Tobacco Plants Coexpressing the Agrobacterium tumefaciens iaaM and iaaH Genes Display Altered Growth and Indoleacetic Acid Metabolism," Plant Physiol., 99, 1062-1069 (1992).
Song et al., "Engineering cherry rootstocks with resistance to Prunus necrotic ring spot virus through RNAi-mediated silencing," Plant Biotechnol. J. 11, 702-708 (2013).
Zhu et al., "Transformation of the apple rootstock M.9/29 with the rolB gene and its influence on rooting and growth," Plant Sci. 160, 433-439 (2001).
Thimann et al., "On the inhibition of bud development and other functions of growth substance in Vicia faba. Proceedings of the Royal Society of London," Series B, Containing Papers of a Biological Character 114, 317-339 (1934).
Van Nocker et al., "Breeding better cultivars, faster: applications of new technologies for the rapid deployment of superior horticultural tree crops.," Horticulture Research, 1, 14022 (2014).
Warschefsky et al., "Rootstocks: diversity, domestication, and impacts on shoot phenotypes," Trends Plant Sci. 21, 418-437 (2016).
Werner et al., "Cytokinin-deficient transgenic *Arabidopsis* plants show multiple developmental alterations indicating opposite functions of cytokinins in the regulation of shoot and root meristem activity," Plant Cell, 15, 2532-2550 (2003).
Werner et al., "Root-specific reduction of cytokinin causes enhanced root growth, drought tolerance, and leaf mineral enrichment in *Arabidopsis* and tobacco," The Plant Cell Online, 22, 3905-3920 (2010).
Xiong et al., "Genome-editing technologies and their potential application in horticultural crop breeding," Horticullure Research, 2, 15019 (2015).
Ye et al., "Field Studies on Dynamic Pollen Production, Deposition, and Dispersion of Glyphosate-Resistant Horseweed (*Conyza canadensis*)," Weed Science, 64, 101-111 (2016).
Yin et al., "Graft-union development: a delicate process that involves cell-cell communication between scion and stock for local auxin accumulation," J Exp Bot, 63, 4219-4232 (2012).
Zhao et al., "Rootstock-to-scion transfer of transgene-derived small interfering RNAs and their effect on virus resistance in nontransgenic sweet cherry," Plant Biotechnol. J. 12, 1319-1328 (2014).

\* cited by examiner

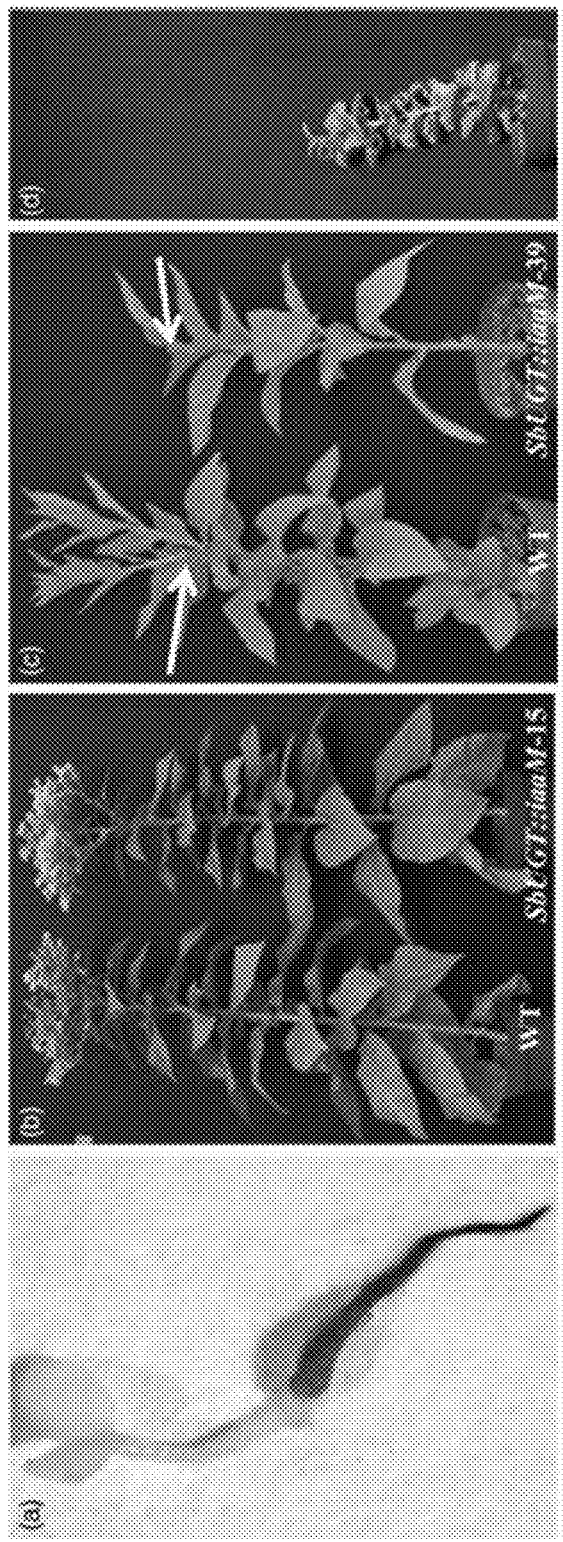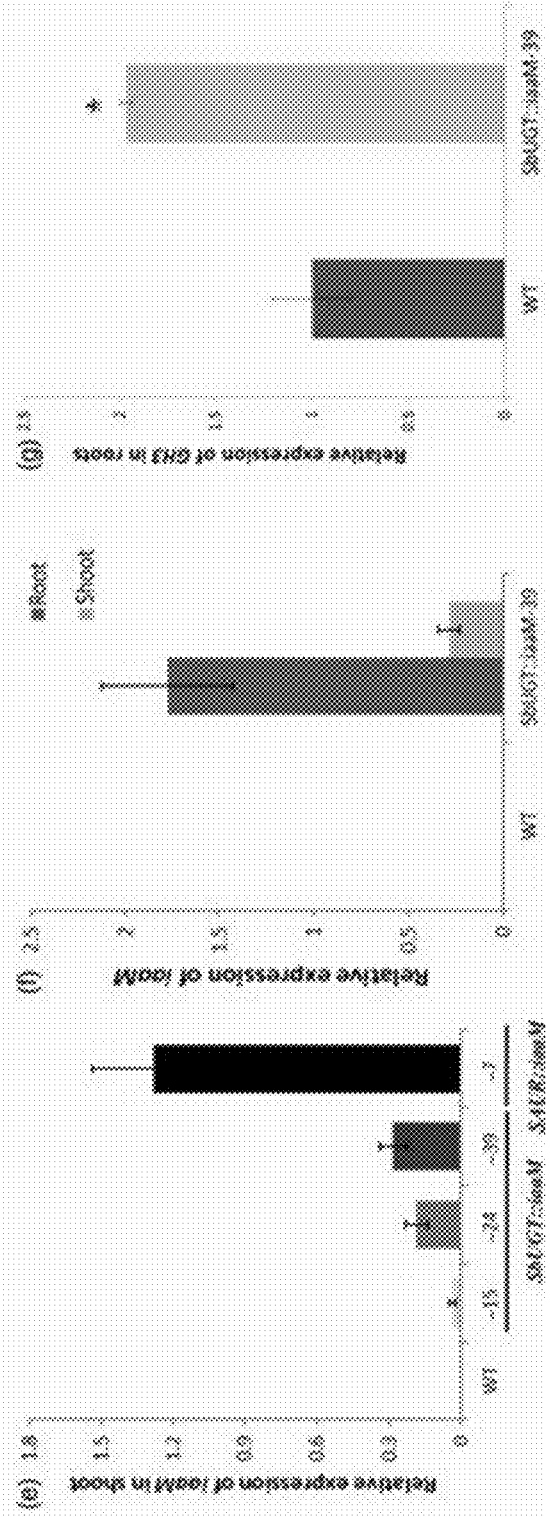
FIGS. 1A-1G

METHOD OF PRODUCING NOVEL ROOTSTOCK PLANTS HAVING IMPROVED GRAFTING TRAITS

CROSS-REFERENCE TO RELATED APPLICATIONS

This application claims priority to U.S. Provisional Application No. 62/508,661, filed May 19, 2017, which is incorporated herein by reference in its entirety.

STATEMENT OF GOVERNMENT INTEREST

This invention was made with government support under federal grant number 2010-33522-21697 awarded by the U.S. Department of Agriculture—NIFA. The U.S. Government has certain rights to this invention.

SEQUENCE LISTING

The instant application contains a Sequence Listing which has been submitted electronically in ASCII format and is hereby incorporated by reference in its entirety. Said ASCII copy, created on May 21, 2018 is named 209670-9017-US02_As_Filed_Sequence_Listing and is 24,148 bytes in size.

FIELD OF INVENTION

Disclosed herein are rootstock plants, and methods of producing the rootstock plants, characterized by improved grafting success, enhanced root growth and other performance parameters.

BACKGROUND

Plant grafting is an important technique for horticultural and silvicultural production. Grafting is a technique whereby tissues of plants are joined so as to continue their growth together. Grafting is most commonly used in asexual propagation of commercially grown plants. The upper part of the combined plant is called the scion while the lower part is called the rootstock. Desirable scions can be grafted on rootstocks that are adapted to certain soil conditions such as wet or dry soils, or that are resistant to soil-borne pests and diseases. In tree fruit production, grafting of scions to rootstocks is used to produce dwarf trees, enhance disease resistance, increase fruit yield and quality, combine production of multiple varieties on a single tree, and enhance fertilization However, many rootstock plants suffer from low grafting success rates, poor rooting, or undesirable lateral bud outgrowth. For example, many woody plant species with excellent rootstock characteristics are difficult to root from stem cuttings. Lateral buds released from rootstock have been shown to negatively affect scion growth and thus grafting success. Also, the undesirable outgrowth of lateral buds from rootstocks after grafting is a common phenomenon. If lateral shoots from rootstock are not suppressed or removed, healing of the graft union can be adversely affected and rootstock's lateral shoots compete with scions for light and nutrients, reducing the rate of grafting success and scion growth. Chemical treatments or manual removal may be used to eliminate lateral shoots from rootstock but these procedures are time consuming and expensive.

Traditional breeding efforts have made impressive progress towards improving rootstock performance in numerous plant species, but continued improvement remains limited to selection of existing traits within the gene pool of rootstock cultivars. Hybridization breeding is also limited, as some elite traits may be lost in the process. Progeny production, through sexual crossing and subsequent selection, is a lengthy and labor-intensive process that can take a decade to reach fruition. For perennial fruit trees, such as walnut, breeding cycles can be 20-30 years. In contrast to traditional breeding, transgenic plant technology can be used to introduce completely new traits into rootstock lines and at a much faster rate, sometimes within months. There is a need for rootstock plants characterized by improved grafting success, enhanced root growth and other performance parameters, as well as a need for methods of making and using said rootstock plants.

SUMMARY

The present invention is directed to a transgenic rootstock plant comprising a first isolated nucleic acid encoding an auxin synthesis-related gene and/or a second isolated nucleic acid encoding a cytokinin degradation-related gene, wherein the first isolated nucleic acid is operably linked to a heterologous root-specific promoter and the second isolated nucleic acid is operably linked to a heterologous root-specific promoter.

The present invention is directed to a method of producing a transgenic rootstock plant having enhanced grafting traits and/or enhanced rooting capacity. The method comprises: a) introducing into a plant cell a first isolated nucleic acid encoding an auxin synthesis-related gene, wherein the first isolated nucleic acid is operably linked to a heterologous root-specific promoter, and/or a second isolated nucleic acid encoding an cytokinin degradation-related gene, wherein the second isolated nucleic acid is operably linked to a heterologous root-specific promoter; and b) regenerating the transformed plant cell to produce a transgenic rootstock plant.

The present invention is directed to a method of producing a transgenic rootstock plant having enhanced grafting traits and/or enhanced rooting capacity. The method comprises: a) obtaining a first transgenic plant comprising a first isolated nucleic acid encoding an auxin synthesis-related gene, wherein the first isolated nucleic acid is operably linked to a heterologous root-specific promoter; b) obtaining a second transgenic plant comprising a second isolated nucleic acid encoding an cytokinin degradation-related gene, wherein the second isolated nucleic acid is operably linked to a heterologous root-specific promoter; and c) generating a cross between the first transgenic plant and the second transgenic plant to produce the transgenic rootstock plant.

The present invention is directed to a transgenic rootstock plant produced by said methods.

The present invention is directed to a method of producing a grafted plant. The method comprises contacting said transgenic rootstock plant with a scion.

BRIEF DESCRIPTION OF THE DRAWINGS

FIGS. 1A-1C show root-predominant expression of an auxin biosynthetic gene (iaaM) inhibited lateral bud release. FIG. 1A shows histochemical staining of GUS activity in a 5-day-old SbUGT::GUS tobacco $T_1$ seedling, showing that the SbUGT promoter was predominantly active in roots. FIG. 1B shows four-month-old wild-type and SbUGT::iaaM-15 tobacco plants, showing that expression of the SbUGT::iaaM gene did not affect growth and developmental patterns of leaves and shoots. FIG. 1C shows three weeks after decapitation, wild-type plants released numerous lateral buds, while the SbUGT::iaaM-39 plants had no lateral buds released from the decapitated shoots; the arrow heads indicate the decapitated shoots of wild-type (left) and SbUGT::iaaM-39 (right) tobacco. FIG. 1D shows a 4-month-old transgenic tobacco plant overexpressing the iaaM gene under the control of a shoot and leaf tissue active promoter (SAUR), displaying strong auxin-overproducing phenotypes, reduced shoot elongation and leaf epinasty. FIG. 1E shows expression levels of the iaaM gene in shoot tissues of 2-month-old SbUGT::iaaM and SAUR::iaaM tobacco plants. FIG. 1F shows relatively high expression of the iaaM gene in roots but low expression in shoots was observed in the 2-month-old SbUGT::iaaM-39 plant line. FIG. 1G shows expression level of the auxin-responsive GH3 gene was enhanced in roots of SbUGT::iaaM-39 line. Asterisks (*) represent significant differences between wild-type and SbUGT::iaaM-39 tobacco using two-tailed Student's t-test with the pooled variance (P<0.05). Bars represent standard errors.

FIG. 2A shows two weeks after grafting, WT/WT grafts had released lateral buds and scion growth was inhibited. FIG. 2B shows if WT/WT grafts' lateral buds were manually removed from the rootstock stumps, scions grew vigorously. FIG. 2C shows WT/iaaM grafts had no lateral buds released from the rootstock stumps, and scions grew vigorously. FIG. 2D shows two months after grafting, WT/iaaM grafts had normal growth similar to WT/WT with lateral buds removed from rootstock stumps. FIG. 2E shows two weeks following decapitation, scions of WT/iaaM had normal lateral buds release similar to the scions of WT/WT grafts, showing that increase in auxin in rootstock did not affect normal growth and development of the scions. Circles show scions. Arrow heads indicate released lateral buds. S: scion. L: lateral bud. R: rootstock.

FIG. 3A shows stem cuttings with shoot tips of wild-type, SbUGT::iaaM-39 (iaaM) and SbUGT::iaaM-39/SbUGT::CKX-64 (iaaM+CKX) hybrid plant after being rooted in fritted clay medium for 10 days, showing that the iaaM gene expression promotes root initiation. FIG. 3B shows six-week-old wild-type. FIG. 3C shows six-week-old iaaM plants. FIG. 3D shows six-week-old iaaM+CKX plants. FIG. 3E shows stem cuttings of SbUGT::CKX-64 (CKX) plants after being cultured on a MS medium for 3 weeks, showing more and longer roots than wild type. FIG. 3F shows significant reduced zeatin contents observed in the roots of CKX plants when compared to wild-type plants. FIG. 3G shows eight-day-old progeny seedlings from the crossings of: iaaM or CKX to wild type, self-crossed wild type and iaaM to CKX. The results showed that auxin-mediated reduction in root growth was neutralized with expression of the CKX gene in roots. FIG. 3H shows effects of the iaaM and CKX gene expression on primary root length. Asterisks (*) represent significant differences compared to wild type using two-tailed Student's t-test with the pooled variance (P<0.05). Bars represent standard errors.

FIG. 4A shows WT/WT grafts three weeks after grafting. FIG. 4B shows WT/iaaM grafts three weeks after grafting. FIG. 4C shows WT/iaaM+CKX grafts three weeks after grafting. FIG. 4D shows WT/CKX three weeks after grafting. S: scion. L: lateral bud. R: rootstock.

FIG. 5A shows a graft union between a wild-type (WT) scion and a WT rootstock (left panel) and a graft union between a WT scion and iaaM rootstock (right panel). FIG. 5B shows the junctions between scions and rootstocks (see arrows) in the graft union between a WT scion and a WT rootstock (left panel) and graft union between a WT scion and iaaM rootstock (right panel).

DETAILED DESCRIPTION

Figures 2A, 2B, 2C, 2D, 2E:
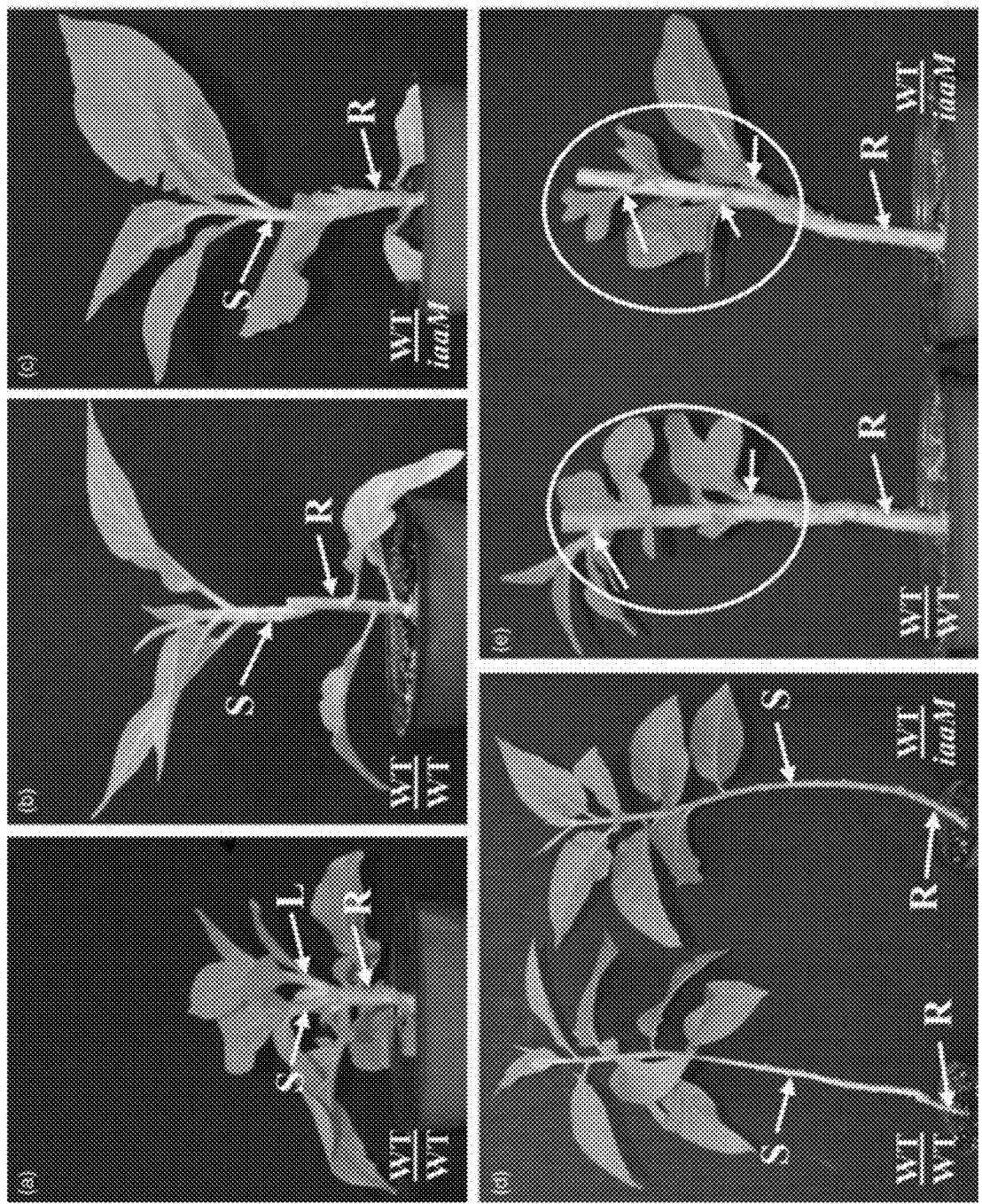
FIGS. 2A-2E show using SbUGT::iaaM-39 plants as rootstock led to inhibited lateral bud release from rootstock stumps and vigorous scion growth.

The present disclosure describes rootstock plants with improved rootstock characteristics and methods of generating and using said rootstock plants. The disclosed plant rootstocks have improved root growth, as well as other performance parameters that allow for improved grafting success, such as inhibited lateral bud outgrowth, enhanced grafting success rate and improved root initiation. The disclosed rootstock plants include a transgene related to auxin synthesis and/or a transgene related to cytokinin degradation. A root-specific gene promoter is operably linked to the transgenes to control the expression to the roots without affecting the growth and development of the above-ground plant parts, which is highly desirable for propagation of rootstock plants. Overproduction of auxins enhances grafting, however overproducing auxin in the whole plant lead to reduced root and stem growth and abnormal leaf development. The combined use of the auxin-overproducing and cytokinin-inactivating genes expressed in roots represents an excellent strategy for rootstock improvement. For example, the differential expression of the iaaM and CKX genes can result in inhibition of lateral bud release from the rootstock, improved grafting success rates and enhanced root initiation and root biomass.

The unique combination and use of an auxin synthesis-related gene, a cytokinin degradation-related gene, and root-specific or root-predominant promoter sequence is shown herein to produce plants having at least three beneficial traits: improved grafting success rate; elimination of the need to remove lateral buds growing from rootstocks; and enhanced root initiation and growth. These three beneficial traits were unexpected and the benefits can lead to reduced labor and production costs for commercial growers in the horticulture and silviculture industries. The combined use of these two genes and the root specific gene promoter removes the negative effect of auxin overproduction on root growth and the negative effect of cytokinin degradation on shoot growth. It was unexpected that overproducing auxin can neutralize the negative effects of reduction in cytokinins.

The disclosed rootstock plants are produced by specifically expressing an auxin synthesis-related gene, such as tryptophan-2-mono oxygenase gene (iaaM) from *Agrobacterium tumafaciens*, and/or a cytokinin-degradation related gene, such as cytokinin oxidase 2 gene from *Arabidopsis thaliana*, in the root of the rootstock plants using a root-specific or root-predominant promoter. Expressing the auxin synthesis-related gene in the roots increases the auxin levels in the roots of the rootstock plants. Transgenic plants expressing the auxin synthesis-related gene in roots, when used as a rootstock, displayed inhibited lateral bud outgrowth, enhanced grafting success rate and improved root initiation.

As high auxin levels in roots can reduce root elongation, root elongation and biomass of the rootstock plant was increased by expressing a cytokinin-degradation related gene in the root as well. Transgenic plants expressing the cytokinin-degradation related gene alone enhances root initiation and growth. Plants having both an auxin synthesis-related gene and a cytokinin-degradation related gene expressed in the root surprising displayed enhanced root elongation and biomass, as the expression of the cytokinin degradation-related gene neutralized the negative effects of higher levels of auxin on root elongation. The simultaneous expression of both the auxin synthesis-related gene and cytokinin degradation-related gene in rootstock did not disrupt normal growth and developmental patterns in wild-type scions.

Although transgenic technology provides a powerful tool for improving plants, such as crops, gene flow and food safety concerns over transgenic plants have impeded its utilization in the horticultural and forestry industries. The methods and plants disclosed herein to combine non-transgenic scions with transgenic rootstock having an auxin synthesis-related transgene and/or a cytokinin degradation-related transgene may encounter less public opposition because fruits, seeds and pollen grains produced from scion shoots are non-transgenic in origin. The transgenic approach presented here may also provide an excellent tool to suppress lateral bud release from rootstock, improve grafting success rates and also reduce the costs associated with chemical or manual removal of lateral buds

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used throughout the specification and the claims, the following terms have the following meanings:

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Construct" as used herein refers to a double-stranded, recombinant nucleic acid fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

The term "control" as used herein in the context of a control plant or control plant cells means a plant or plant cells in the auxin synthesis-related gene and/or cytokinin degradation-related gene each operably linked to a root-specific or root-predominant promoter has not been introduced and so it can provide a comparison with a plant in which the auxin synthesis-related gene and/or cytokinin degradation-related gene each operably linked to a root-specific or root-predominant promoter has been introduced.

As used herein, a "control plant" is a plant that is substantially equivalent to a test plant or modified plant in all parameters with the exception of the test parameters. For example, when referring to a plant into which a polynucleotide according to the present invention has been introduced, in certain embodiments, a control plant is an equivalent plant into which no such polynucleotide has been introduced. In certain embodiments, a control plant is an equivalent plant into which a control polynucleotide has been introduced. In such instances, the control polynucleotide is one that is expected to result in little or no phenotypic effect on the plant. The control plant may comprise an empty vector. The control plant may correspond to a wild-type plant. The control plant may be a null segregant wherein the T1 segregant no longer possesses the transgene.

As used herein, the phrase "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein. In some embodiments, the present invention provides genotypes derived from the plants produced by the compositions, methods, and systems described herein. As used herein, the term "genotype" refers to the genetic makeup of an individual cell, cell culture, tissue, organism (e.g., a plant), or group of organisms. In some embodiments, the present invention provides clones derived from the plants produced by the compositions, methods, and systems described herein.

"Endogenous gene" as used herein refers to a gene that originates from the genome of the organism and has not undergone a change, such as a loss, gain, or exchange of genetic material. An endogenous gene undergoes normal gene transmission and gene expression.

"Enhancer sequences" as used herein refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

"Expression" as used herein refers to the production of a functional product. For example, expression of a nucleic acid fragment may refer to transcription of the nucleic acid fragment (e.g., transcription resulting in mRNA or functional RNA) and/or translation of mRNA into a precursor or mature protein. "Overexpression" refers to the production of a gene product in transgenic organisms that exceeds levels of production in a null segregating (or non-transgenic) organism from the same experiment.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetically modified" or "GM" as used interchangeably herein refers to an organism or crop containing genetic material that has been artificially altered so as to produce a desired characteristic.

As used herein, the term "grafted plant" refers to a plant comprising a rootstock and a scion, wherein the scion is grafted onto the rootstock by any method known in the art. A "graft" is produced by connecting two pieces of living plant issue together so that they will unite and form a functional plant and subsequently grow as one new plant. The "graft union" is the place on the stem of a plant where the scion is joined to the rootstock.

"Heterologous" as used herein with respect to a sequence means a sequence that originates from a foreign species, or, if from the same species, is substantially modified from its native form in composition and/or genomic locus by deliberate human intervention.

The terms "homology" or "similarity" as used herein refer to the degree of sequence similarity between two polypeptides or between two nucleic acid molecules compared by sequence alignment. The degree of homology between two discrete nucleic acid sequences being compared is a function of the number of identical, or matching, nucleotides at comparable positions.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as ClustalW, ClustalX, BLAST, FASTA or Smith-Waterman.

The term "increase" or "increased" as used herein, refers to an increase of from about 10% to about 99%, or an increase of at least 10%, at least 20%, at least 25%, at least 30%, at least 40%, at least 50%, at least 60%, at least 70%, at least 75%, at least 80%, at least 90%, at least 95%, at least 98%, at least 99%, at least 100%, at least 150%, or at least 200% or more or more of a quantity or an activity, such as but not limited to auxin or cytokinin levels and/or root growth, biomass, grafting success rate, or root length.

The term "introduced" as used herein means providing a nucleic acid (e.g., expression construct) or protein into a cell. Introduced includes reference to the incorporation of a nucleic acid into a eukaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The terms "isolated," "purified" or "biologically pure" as used herein refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" as used herein denotes that a nucleic acid or protein gives rise to essentially one band in an electrophoretic gel. Particularly, it means that the nucleic acid or protein is at least 85% pure, more preferably at least 95% pure, and most preferably at least 99% pure.

Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. "Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

The term "plant" as used herein refers to any plant at any stage of its life cycle or development, and its progenies. "Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores. Preferred species, cultivars, hybrids and varieties of tobacco plant are described herein.

"Polynucleotide", "nucleic acid sequence", "nucleotide sequence", or "nucleic acid fragment" are used interchangeably herein to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. A polynucleotide can be, without limitation, a genomic DNA, complementary DNA (cDNA), mRNA, or antisense RNA or a fragment(s) thereof. Moreover, a polynucleotide can be single-stranded or double-stranded, nucleic acid that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid (PNA). Generally, polynucleotides can be assembled from isolated or cloned fragments of cDNA, genomic DNA, oligonucleotides, or individual nucleotides, or a combination of the foregoing. Although the polynucleotide sequences described herein are shown as DNA sequences, the sequences include their corresponding RNA sequences, and their complementary (for example, completely complementary) DNA or RNA sequences, including the reverse complements thereof.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Promoter" as used herein means a synthetic or naturally-derived molecule which is capable of conferring, activating or enhancing expression of a nucleic acid in a cell. A "promoter" refers to a nucleic acid element/sequence, typically positioned upstream and operably-linked to a double-stranded nucleic acid fragment. Promoters can be derived entirely from regions proximate to a native gene of interest, or can be composed of different elements derived from different native promoters or synthetic nucleic acid segments. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents.

"Recombinant" as used herein refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" as used herein refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein.

"Regulatory sequences" and "regulatory elements" as used interchangeably herein refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

A "root-specific promoter" or "root-predominant promoter" as used interchangeably herein refers to a promoter that is transcriptionally active predominantly in plant roots, substantially to the exclusion of any other parts of a plant, whilst still allowing for any leaky expression in these other plant parts.

"Rootstock" and "rootstock plant" as used interchangeably herein refer to a stock for grafting comprising the root part of a plant. The rootstock is the base and root portion of a grafted plant. The rootstock is the belowground or lower part of a plant, sometimes including part of the stem and some branches that will form the root system of the new plant.

"Scion" as used herein refers to a detached living portion of a plant designed or prepared for union with a stock in grafting, usually supplying solely or predominantly aerial parts to the graft. The scion is the aerial part of a plant that forms the crown of the new plant. The scion is typically the flowering and/or fruiting part of the plant that is grafted onto rootstock to produce a plant.

The term "substantial identity" of polynucleotide sequences means that a polynucleotide comprises a sequence that has at least 25% sequence identity compared to a reference sequence as determined using the programs described herein; preferably BLAST using standard parameters, as described. Alternatively, percent identity can be any integer from 25% to 100%. More preferred embodiments include polynucleotide sequences that have at least about: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% sequence identity compared to a reference sequence. These values can be appropriately adjusted to determine corresponding identity of proteins encoded by two nucleotide sequences by taking into account codon degeneracy, amino acid similarity, reading frame positioning, and the like. Accordingly, polynucleotides of the present invention encoding a protein of the present invention include nucleic acid sequences that have substantial identity to the nucleic acid sequences that encode the polypeptides of the present invention. Polynucleotides encoding a polypeptide comprising an amino acid sequence that has at least about: 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference polypeptide sequence are also preferred.

The term "substantial identity" of amino acid sequences (and of polypeptides having these amino acid sequences) normally means sequence identity of at least 40% compared to a reference sequence as determined using the programs described herein; preferably BLAST using standard parameters, as described. Preferred percent identity of amino acids can be any integer from 40% to 100%. More preferred embodiments include amino acid sequences that have at least about: 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference sequence. Polypeptides that are "substantially identical" share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

"Target plant" as used herein refers to a plant or tree that will be transformed with recombinant genetic material not normally found in plants or trees of this type and which will be introduced into the plant in question (or into progenitors of the plant) by human manipulation.

"Transcription terminator", "termination sequences", or "terminator" as used herein refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Transgene" as used herein refers to a gene or genetic material containing a gene sequence that has been isolated from one organism, such as one plant or plant cell, and is introduced into a different organism, such as a different plant or plant cell. This non-native segment of DNA may retain the ability to produce RNA or protein in the transgenic organism, such as the transgenic plant, or it may alter the normal function of the transgenic organism's genetic code. The introduction of a transgene has the potential to change the phenotype of an organism, such as a plant.

"Transgenic" as used herein refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transgenic plant" as used herein includes reference to a plant which comprises within its genome a heterologous polynucleotide, i.e., a plant or tree that contains recombinant genetic material not normally found in plants or trees of this type and which has been introduced into the plant in question (or into progenitors of the plant) by human manipulation. For example, the heterologous polynucleotide is stably integrated within the genome such that the polynucleotide is passed on to successive generations. The heterologous polynucleotide may be integrated into the genome alone or as part of a recombinant DNA construct. The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems etc. "Transgenic plant" also includes reference to plants which comprise more than one heterologous polynucleotide within their genome. Each heterologous polynucleotide may confer a different trait to the transgenic plant. A "transgenic rootstock plant" as used herein refers to the target plant that is transformed with and comprises within its genome a heterologous polynucleotide and will be used as a rootstock plant.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change.

The term "variety" as used herein refers to a population of plants that share constant characteristics which separate them from other plants of the same species. While possessing one or more distinctive traits, a variety is further characterized by a very small overall variation between individuals within that variety. A variety is often sold commercially.

"Vector" as used herein means refers to a nucleic acid vehicle that comprises a combination of nucleic acid components for enabling the transport of nucleic acid, nucleic acid constructs and nucleic acid conjugates and the like. A vector may be a viral vector, bacteriophage, bacterial artificial chromosome or yeast artificial chromosome. A vector may be a DNA or RNA vector. Suitable vectors include episomes capable of extra-chromosomal replication such as circular, double-stranded nucleic acid plasmids; linearized double-stranded nucleic acid plasmids; and other vectors of any origin. For example, the vector may encode an auxin synthesis-related gene and/or cytokinin degradation-related gene each operably linked to a root-specific or root-predominant promoter comprising the amino acid sequence of any one of SEQ ID NOs: 1, 2, 4, 6 or 7. An "expression vector" as used herein is a nucleic acid vehicle that comprises a combination of nucleic acid components for enabling the expression of nucleic acid, nucleic acid constructs and nucleic acid conjugates and the like. Suitable expression vectors include episomes capable of extra-chromosomal replication such as circular, double-stranded nucleic acid plasmids; linearized double-stranded nucleic acid plasmids; and other functionally equivalent expression vectors of any origin. An expression vector comprises at least a promoter positioned upstream and operably-linked to a nucleic acid, nucleic acid constructs or nucleic acid conjugate, as defined below.

All documents cited herein and the following listed documents that are attached hereto for submission, all referenced publications cited therein, and the descriptions and information contained in these documents are expressly incorporated herein in their entirety to the same extent as if each document or cited publication was individually and expressly incorporated herein:

While the invention has been described with reference to preferred embodiments, it will be understood by those skilled in the art that various changes may be made and equivalents may be substituted for the elements thereof without departing from the scope of the invention. In addition, many modifications may be made to adapt the teaching of the invention to particular use, application, manufacturing conditions, use conditions, composition, medium, size, and/or materials without departing from the essential scope and spirit of the invention.

While various aspects and embodiments have been disclosed herein, other aspects and embodiments will be apparent to those skilled in the art. The various aspects and embodiments disclosed herein are for purposes of illustration and are not intended to be limiting of the true scope of the invention disclosed herein. It is also to be understood that the terminology used herein is for the purpose of describing particular embodiments only, and is not intended to be limiting. Since many modifications, variations, and changes in detail can be made to the described examples, it is intended that all matters in the preceding description and shown in the accompanying figures be interpreted as illustrative and not in a limiting sense. All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and words of a similar nature in the context of describing the improvements disclosed herein (especially in the context of the following claims) are to be construed to cover both the singular and the plural, unless otherwise indicated herein or clearly contradicted by context. Further, it should further be noted that the terms "first," "second," and the like herein do not denote any order, quantity, or relative importance, but rather are used to distinguish one element from another. The modifier "about" used in connection with a quantity is inclusive of the stated value and has the meaning dictated by the context (e.g., it includes, at a minimum the degree of error associated with measurement of the particular quantity).

All methods described herein can be performed in any suitable order unless otherwise indicated herein or otherwise clearly contradicted by context. The use of any and all examples, or exemplary language (e.g., "such as"), is intended merely to better illustrate the invention and does not pose a limitation on the scope of the invention or any embodiments unless otherwise claimed.

2. TRANSGENIC ROOTSTOCK PLANTS AND METHODS OF PRODUCING SAID PLANTS

The present disclosure relates to transgenic rootstock plants having enhanced grafting traits and/or enhanced rooting capacity. The transgenic rootstock plants has a first isolated nucleic acid encoding an auxin synthesis-related gene and/or a second isolated nucleic acid encoding a cytokinin degradation-related gene, wherein the first isolated nucleic acid is operably linked to a heterologous root-specific promoter and the second isolated nucleic acid is operably linked to a heterologous root-specific promoter. In some embodiments, the enhanced grafting traits and/or enhanced rooting capacity can include inhibited lateral bud outgrowth, enhanced grafting success rate, improved root biomass and improved root initiation, as compared to a control plant. In some embodiments, the transgenic rootstock plant includes a first isolated nucleic acid encoding an auxin synthesis-related gene or a second isolated nucleic acid encoding a cytokinin degradation-related gene. In some embodiments, the transgenic rootstock plant includes a first isolated nucleic acid encoding an auxin synthesis-related gene and a second isolated nucleic acid encoding a cytokinin degradation-related gene.

The present disclosure relates to methods of producing a transgenic rootstock plant having enhanced grafting traits and/or enhanced rooting capacity. The method includes: a) introducing into a plant a first isolated nucleic acid encoding an auxin synthesis-related gene, wherein the first isolated nucleic acid is operably linked to a heterologous root-specific promoter, and/or a second isolated nucleic acid encoding an cytokinin degradation-related gene, wherein the second isolated nucleic acid is operably linked to a heterologous root-specific promoter; and b) regenerating the transformed plant cell to produce a transgenic rootstock plant. In some embodiments, the transgenic rootstock plant includes a first isolated nucleic acid encoding an auxin synthesis-related gene or a second isolated nucleic acid encoding a cytokinin degradation-related gene. In some embodiments, the transgenic rootstock plant includes a first isolated nucleic acid encoding an auxin synthesis-related gene and a second isolated nucleic acid encoding a cytokinin degradation-related gene.

In an alternative embodiment, the method includes: a) obtaining a first transgenic plant comprising a first isolated nucleic acid encoding an auxin synthesis-related gene, wherein the first isolated nucleic acid is operably linked to a heterologous root-specific promoter; b) obtaining a second transgenic plant comprising a second isolated nucleic acid encoding an cytokinin degradation-related gene, wherein the second isolated nucleic acid is operably linked to a heterologous root-specific promoter; and c) generating a cross between the first transgenic plant and the second transgenic plant thereby producing the transgenic rootstock plant. The present disclosure also relates to transgenic rootstock plants produced by the disclosed methods.

The auxin synthesis-related genes, such as iaaM genes, the cytokinin degradation-related genes, such as CKX genes, and the root-predominant or root-specific promoters for use in the disclosed methods may naturally occur in species different from the plant species for which improved rootstock is desired. In preferred embodiments at least one of the genes or promoters is from such a heterologous source.

a) Auxin Synthesis-Related Gene

The auxin synthesis-related gene can be a gene involved in synthesizing auxin either directly or indirectly. Lateral branching in plants is regulated by interactions between the phytohormones indole-3-acetic acid (IAA, auxin), cytokinin and strigolactone. Apically derived auxin inhibits lateral bud outgrowth and cytokinin directly or indirectly stimulates bud outgrowth. Insertion of the *Agrobacterium* gene iaaM gene that encodes a tryptophan-2-monooxygenase into plants can convert tryptophan to indole-3-acetamide. Indole-3-acetamide is then slowly converted by endogenous hydrolases to the active phytohormone indole-3-acetic acid.

While the examples disclosed herein and in the attached Documents are specific to the iaaM gene as a gene whose overexpression leads to increased auxin levels, those of skill in the art can apply the disclosed methods and approaches to achieve overexpression of any other gene whose overexpression leads to increased auxin levels in a plant of interest.

In some embodiments, the gene for auxin synthesis or auxin synthesis-related gene is an iaaM gene. In some embodiments, the gene for auxin synthesis or auxin synthesis-related gene is a tryptophan-2-monooxygenase gene from *Agrobacterium tumefaciens*. In some embodiments, the iaaM gene comprises a polynucleotide sequence of SEQ ID NO: 2, or substantial variant thereof.

b) Cytokinin Degradation-Related Gene

The cytokinin degradation-related gene can be a gene involved in degrading cytokinin either directly or indirectly. For example, cytokinin dehydrogenase (CKX) degrades the phytohormone cytokinin. While the examples disclosed herein and in the attached Documents are specific to the CKX gene as a gene whose overexpression leads to increased degradation of cytokinin, those of skill in the art can apply the disclosed methods and approaches to achieve overexpression of any other gene whose overexpression leads to increased degradation of cytokinin in a plant of interest.

In some embodiments, the gene for cytokinin degradation or cytokinin degradation-related gene is a CKX gene. In some embodiments, the gene for cytokinin degradation or cytokinin degradation-related gene is *Arabidopsis* cytokinin oxidase 2 gene. In some embodiments, the CKX gene comprises a polynucleotide sequence of SEQ ID NO: 4, or substantial variant thereof.

c) Root-Specific Promoter or Root-Predominant Promoter

The root-predominant or root-specific promoter that is operably linked to the auxin synthesis-related gene and/or cytokinin degradation-related gene coding sequence may be not natively associated with the polynucleotide encoding the auxin synthesis-related gene and/or cytokinin degradation-related gene. In some embodiments, the root-specific promoter can include SbUGT promoter sequence (SEQ ID NO: 1), RCc3 promoter (Plant Mol Biol. 1995 January; 27(2): 237-48), *Arabidopsis* PHT1 promoter, Medicago phosphate transporter promoter, *Arabidopsis* Pyk10 promoter, root-expressible genes promoter, tobacco auxin-inducible gene promoter, β-tubulin promoter, tobacco root-specific genes promoter, BTG-26 *Brassica napus* promoter, *B. napus*

G1-3b gene promoter, SbPRP1 promoter, LRX1 promoter, LeAMT1 (tomato) promoter, LeNRT1-1 (tomato) promoter, class I patatin gene (potato) promoter, KDC1 (*Daucus carota*) promoter, TobRB7 gene promoter, OsRAB5a (rice) promoter, ALF5 (*Arabidopsis*) promoter, and NRT2; 1Np (*N. plumbaginifolia*), the root-specific glutamine synthetase gene promoters. While the examples disclosed herein and in the attached Documents are specific to the SbUGT promoter as a root-predominant or root-specific promoter, those of skill in the art can apply the disclosed methods and approaches to the use of any other root-predominant or root-specific promoter in a plant of interest. Different promoter sequences of various lengths can be used as well.

In some embodiments, the heterologous root-specific promoter is a SbUGT promoter. In some embodiments, the SbUGT promoter comprises a polynucleotide sequence of SEQ ID NO: 1, or substantial variant thereof.

3. METHODS OF USING THE TRANSGENIC ROOTSTOCK PLANT TO PRODUCE A GRAFTED PLANT

The disclosed rootstock plants can be used in a method for producing a grafted plant. The method includes contacting the transgenic rootstock plant with a scion. The disclosed rootstock plants can be used by various type of grafting. The grafting of a scion upon a rootstock is a common horticultural practice used for many years in the propagation of woody plants. The scion contains the desired genes to be duplicated in future production by the stock/scion plant. In some embodiments, the scion can be any plant that has desirable traits and characteristics. In some embodiments, the scion can be the same plant species as the rootstock plant. In some embodiments, the scion can be a wild-type plant. In some embodiments, the scion can be a different plant species as the rootstock.

Once grafted, water and nutrients are transported from the rootstock to the scion to support growth of the scion. Grafting is widely used with a variety of plants species, to improve the horticultural traits of the resulted grafted plant. The method of grafting is typically used when the scion produces the desired agricultural product. Advantageously, some agricultural product produced by the disclosed rootstock plants may not be genetically modified, as the rootstock is the only transgenic part of the plant. In some embodiments, the disclosed rootstock plants can be used to enhance resistances to biotic and abiotic stresses, improving water, and nutrient uptake, or increasing yield.

Grafting is a method of asexual plant propagation widely used in agriculture and horticulture where the tissues of one plant are encouraged to fuse with those of another. Grafting involves combining two independent plant parts into one plant. Such combination may be performed in various ways, including, but not limited to cleft grafting, side grafting, whip grafting, stub grafting, awl grafting, veneer grafting, bark grafting, tongue grafting, splice grafting, tip-cleft grafting, saddle grafting, approach grafting, and budding grafting (patch budding, chip budding, T-budding) (for further details see Garner R. J., The Grafter's Handbook, 5th Ed edition (March 1993) Cassell Academic; ISBN: 0304342742).

For successful grafting to take place, the vascular cambium tissues of the stock and scion plants must be placed in contact with each other. Both tissues must be kept alive until the graft has taken, usually a period of a few weeks. Successful grafting only requires that a vascular connection takes place between the two tissues. A physical weak point often still occurs at the graft, because the structural tissue of the two distinct plants, such as wood, may not fuse.

4. TARGET PLANT

It is expected that the approach and methods disclosed herein can be applied to a wide range of plants for which grafting is commonly used, including but not limited to fruit and nut trees such as apple, peach, plum, pear, citrus, cherry, hazelnut, and filbert; grape vines; woody shrubs such as roses and camellias; trees such as ash, beech, birch, cedar, ornamental cherry, dogwood, fir, honey locust, maple, redbud, spruce and witch hazel. While the examples disclosed herein and in the attached Documents are specific to tobacco, those of skill in the art can apply the disclosed methods and approaches to any type of plant for which improved rootstock characteristics are desired.

The transgenic rootstock plants can be any a wide range of plants for which grafting is commonly used, including but not limited to fruit and nut trees such as apple, peach, plum, pear, citrus, cherry, hazelnut, and filbert; grape vines; woody shrubs such as roses and camellias; trees such as ash, beech, birch, cedar, ornamental cherry, dogwood, fir, honey locust, maple, redbud, spruce and witch hazel. The target plant to be transformed to produce the transgenic rootstock plant may be any plant species. In some embodiments, the target plant is a gymnosperm or angiosperm. In some embodiments, the angiosperm may be a dicot plant. In some embodiments, the target plant is a fruit tree, a nut tree, a woody shrub, a hardwood tree, a softwood tree, a crop plant, or an ornamental plant. In some embodiments, the plant can be a crop plant, such as a fruit, a legume, a vegetable, or a root crop, ornamental plants, or a non-food crop, such as cotton, hemp (*Cannabis sativa*), or oilseed rape (*Brassica napus*). Suitable plant species include, without limitation, soybean (*Glycine max*), *Brassica* sp. (e.g., *Arabidopsis thaliana, Brassica napus, B. rapa*, and *B. juncea*), alfalfa (*Medicago sativa*), sunflower (*Helianthus annuus*), safflower (*Carthamus tinctorius*), tobacco (*Nicotiana tabacum*), potato (*Solanum tuberosum*), peanuts (*Arachis hypogaea*), pea (*Pisum sativum*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), balsam poplar (*Populus balsamifera*) cocoa (*Theobroma cacao*), grape (*Vitis vinifera*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena sativa*), barley (*Hordeum vulgare*), vegetables, ornamentals, and conifers.

a) Citrus Plants

The disclosed rootstock plant can be a citrus tree. A "citrus" is a plant of the genus *Citrus* or a related genus. The *Citrus* genus includes the trees and shrubs of the rue family (Rutaceae). A "mature citrus" flowers and produces fruit.

Citrus greening (HLB) bacteria enter citrus trees via Asian citrus psyllid, which sucks on leaf sap and leaves the bacteria behind. The bacteria then travel to roots and cause damages. Nutrient starvations cause production of thus poor fruit appearing and quality. Most infected trees die within a few years. The greening disease can result in a loss of 30 to 50 percent of trees' fibrous roots before any symptoms can be seen in the above ground portion of the tree.

The use of super root mutants as rootstock with from scions that are infected with HLB-causing bacteria produced new flush that was healthy and completely normal on Murcotts, with no HLB-causing bacteria detected in new growth. Because Murcotts is highly susceptible to HLB, the increased root health and density of the rootstock may lead to mitigate the HLB disease. While increased root health and density are not a cure for HLB, it should help more trees survive and therefore can be used to reduce HLB-caused yield losses of fruits. In some embodiments, the rootstock plant can be a citrus plant. The use of non-transgenic citrus scions and the disclosed rootstock plant that is citrus, such as a transgenic SbUGT::iaaM and SbUGT::CKX citrus rootstock may encounter less public opposition because fruits, seeds and pollen grains produced from scion shoots are non-transgenic.

5. CONSTRUCTS, VECTOR, AND EXPRESSION VECTOR

In certain embodiments, the polynucleotides to be introduced into the target plant are operably linked to the root-specific or root-predominant promoter sequence and may be provided as a construct. As used herein, a polynucleotide is "operably linked" when it is placed into a functional relationship with a second polynucleotide sequence. For instance, a promoter is operably linked to a coding sequence if the promoter is connected to the coding sequence such that it may effect transcription of the coding sequence. In various embodiments, the polynucleotides may be operably linked to at least one, at least two, at least three, at least four, at least five, or at least ten promoters.

The nucleic acid sequences may make up a genetic construct that may be a vector. The vector may be capable of expressing the auxin synthesis-related gene and/or cytokinin degradation-related gene each operably linked to a root-specific or root-predominant promoter in the cell of a target plant. The vector may be recombinant. The vector may comprise heterologous nucleic acid encoding the auxin synthesis-related gene and/or cytokinin degradation-related gene each operably linked to a root-specific or root-predominant promoter. Suitable vectors include plasmids and virus-derived vectors. Vectors known in the art that are suitable for transformation into plants, cloning, and protein expression may be used. The vector may be useful for transfecting cells with nucleic acid encoding the auxin synthesis-related gene and/or cytokinin degradation-related gene each operably linked to a root-specific or root-predominant promoter, which the transformed host cell is cultured and maintained under conditions wherein expression of the auxin synthesis-related gene and/or cytokinin degradation-related gene each operably linked to a root-specific or root-predominant promoter takes place.

The genetic constructs may comprise a nucleic acid sequence that encodes the auxin synthesis-related gene and/or cytokinin degradation-related gene each operably linked to a root-specific or root-predominant promoter disclosed herein. The genetic construct may be present in the cell as a functioning extrachromosomal molecule. The genetic construct may be a linear minichromosome including centromere, telomeres or plasmids or cosmids. The genetic construct may also be part of a genome of a recombinant viral vector, including recombinant cauliflower mosaic virus, recombinant tobacco mosaic virus, and recombinant potato virus X-based vectors. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer an initiation codon, a stop codon, or a polyadenylation signal.

The vector may comprise heterologous nucleic acid encoding the auxin synthesis-related gene and/or cytokinin degradation-related gene each operably linked to a root-specific or root-predominant promoter and may further comprise an initiation codon, which may be upstream of the auxin synthesis-related gene and/or cytokinin degradation-related gene coding sequence and a stop codon, which may be downstream of the auxin synthesis-related gene and/or cytokinin degradation-related gene coding sequence. The initiation and termination codon may be in frame with the auxin synthesis-related gene and/or cytokinin degradation-related gene coding sequence. The vector may also comprise a polyadenylation signal, which may be downstream of the auxin synthesis-related gene and/or cytokinin degradation-related gene coding sequence. The vector may also comprise an enhancer upstream of the auxin synthesis-related gene and/or cytokinin degradation-related gene coding sequence. The enhancer may be necessary for DNA expression. The vector may also comprise a plant origin of replication in order to maintain the vector extrachromosomally and produce multiple copies of the vector in a cell. The vector may also comprise a regulatory sequence, which may be well suited for gene expression in a plant cell into which the vector is administered. The vector may also comprise a reporter gene, such as green fluorescent protein ("GFP") and/or a selectable marker, such as hygromycin ("Hygro").

Coding sequences may be optimized for stability and high levels of expression. In some instances, codons are selected to reduce secondary structure formation of the RNA such as that formed due to intramolecular bonding.

The vector may be expression vectors or systems to produce protein by routine techniques and readily available starting materials including Sambrook et al., 1989, which is incorporated fully by reference. In some embodiments the vector may comprise the nucleic acid sequence encoding the auxin synthesis-related gene and/or cytokinin degradation-related gene each operably linked to a root-specific or root-predominant promoter.

a. Plant Transformation

The polynucleotide encoding the auxin synthesis-related gene and/or cytokinin degradation-related gene each operably linked to a root-specific or root-predominant promoter may be introduced into a plant cell to produce a transgenic rootstock plant. As used herein, "introduced into a plant" with respect to polynucleotides encompasses the delivery of a polynucleotide into a plant, plant tissue, or plant cell using any suitable polynucleotide delivery method. Methods suitable for introducing polynucleotides into a plant useful in the practice of the present invention include, but are not limited to, freeze-thaw method, microparticle bombardment, direct DNA uptake, electroporation, sonication, microinjection, plant virus-mediated, and *Agrobacterium*-mediated transfer to the plant. Any suitable *Agrobacterium* strain, vector, or vector system for transforming the plant may be employed according to the present invention. In certain embodiments, the polynucleotide is introduced using at least one of stable transformation methods, transient transformation methods, or virus-mediated methods.

By "stable transformation" is intended that the nucleotide construct introduced into a plant integrates into the genome of the plant and is capable of being inherited by progeny thereof. For example, the introduced nucleotide and/or linked selectable marker gene may be segregated away in subsequent plant generations using conventional breeding techniques.

By "transient transformation" is intended that a nucleotide construct introduced into a plant does not integrate into the genome of the plant. A plant or plant cell may also be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions. For example, plant cells may be initially be transformed with the auxin synthesis-related gene and/or cytokinin degradation-related gene each operably linked to a root-specific or root-predominant promoter lacking a selectable marker and may be grown on media lacking a selection agent. Under such conditions, a fraction of the treated cells will acquire the auxin synthesis-related gene and/or cytokinin degradation-related gene each operably linked to a root-specific or root-predominant promoter and will express the auxin synthesis-related gene and/or cytokinin degradation-related gene transiently without integrating the auxin synthesis-related gene and/or cytokinin degradation-related gene into the genome. Because it does not account for transformation efficiency, this latter transformation procedure requires that a greater number of treated cells be screened to obtain the desired genome modification.

Suitable methods of introducing nucleotide sequences into plant cells and subsequent insertion into the plant genome include microinjection (Crossway et al., Biotechniques 4:320-334 (1986)), electroporation (Riggs et al., Proc. Natl. Acad. Sci. USA 83:5602-5606 (1986)), Agrobacterium-mediated transformation (U.S. Pat. Nos. 5,981,840 and 5,563,055), direct gene transfer (Paszkowski et al., EMBO J. 3:2717-2722 (1984)), and ballistic particle acceleration (see, for example, U.S. Pat. Nos. 4,945,050; 5,879,918; 5,886,244; 5,932,782; Tomes et al., in Plant Cell, Tissue, and Organ Culture: Fundamental Methods, ed. Gamborg and Phillips (Springer-Verlag, Berlin) (1995); and McCabe et al., Biotechnology 6:923-926 (1988)), all of which are herein incorporated by reference in their entireties.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media and/or root induction media. See, for example, McCormick et al., Plant Cell Reports 5:81-84 (1986). These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. Thus as used herein, "transformed seeds" refers to seeds that contain the nucleotide construct stably integrated into the plant genome.

6. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present invention has multiple aspects, illustrated by the following non-limiting examples.

Example 1

Materials and Methods

Plasmid construction. The SbUGT promoter sequence, −102 to +86 relative to the transcription start site of a flavonoid glycosyltransferase gene from *Scutellaria barbata* (SEQ ID NO: 1) was synthesized and inserted upstream of the GusPlus-coding region in a pCAMBIA-GusPlus-nptII plasmid to create the SbUGT::GUS construct. The SbUGT promoter sequence as well as the coding region of iaaM (a tryptophan-2-monooxygenase gene from *Agrobacterium tumefaciens*) (nucleotide and amino acid sequences are SEQ ID NO: 2 and SEQ ID NO: 3, respectively) or AtCKX2 (*Arabidopsis* cytokinin oxidase 2 gene) (nucleotide and amino acid sequences are SEQ ID NO: 4 and SEQ ID NO: 5, respectively) were synthesized as one fragment and sub-cloned into a pCAMBIA-GusPlus-nptII plasmid to create the SbUGT::iaaM (SEQ ID NO: 6) or SbUGT::CKX construct (SEQ ID NO: 7), respectively.

Tobacco transformation and molecular confirmation of transgenic plants. Plasmid vector of SbUGT::GUS, SbUGT::iaaM or SbUGT::CKX construct was introduced into *Agrobacterium tumefaciens* strain EHA105, and the resulting bacteria were used to transform *Nicotiana tabacum* cv. xanthi. Tobacco leaf disc transformation was performed as described previously (Zheng et al., Plant Cell Rep. 26, 1195-1203 (2007)).

Genomic DNA was extracted from the leaves of putative transgenic plants using a modified CTAB protocol (Porebski et al., Plant Mol. Biol. Rep. 15, 8-15 (1997)). Extracted DNA was fractioned on a 0.8% (w/v) agarose gel in order to separate genomic DNA from any potential contamination from Ti-plasmids. The purified genomic DNA was gel-extracted and then used as template for PCR. The primer pair iaaM-F (5'-TTCTCCGAAGCACAACTA-3' (SEQ ID NO: 8)) and iaaM-R (5'-GCCCACCTAATGTCTCC-3' (SEQ ID NO: 9)) was used to amplify a 797-bp fragment from the iaaM gene within the T-DNA region of the Ti-plasmid. The primer pair CKX-F (5'-CGTTATGGGTGGATGTG-3' (SEQ ID NO: 10)) and CKX-R (5'-TAAGCCAAGGATGAGGA-3' (SEQ ID NO: 11)) was used to amplify a 711-bp fragment of the CKX gene within the T-DNA region of the Ti-plasmid. PCR reaction solution was 20 µL aliquot containing 1×PCR buffer (Takara, Japan), 1.5 mM $MgCl_2$, 0.2 mM dNTPs, 0.2 µL e2TAK DNA polymerase (Takara, Japan), 0.25 µM of each primer and 500 ng DNA. The amplification started with an initial denaturation step at 98° C. for 5 min, followed by 35 cycles of 98° C. for 10 s, 60-65° C. for 5 s and 72° C. extension plus a final extension at 72° C. for 10 min.

Histochemical GUS activity assays. $T_0$ SbUGT::GUS tobacco plants were self-pollinated to produce $T_1$ progeny seeds. Five-day-old $T_1$ seedlings were incubated in X-gluc solution at 37° C. overnight for histochemical GUS activity staining. The histochemical assay staining solution contained 100 mM potassium phosphate buffer, pH 7.0, 10 mM $Na_2EDTA$, 0.5 mM $K_3Fe(CN)_6$, 0.5 mM $K_4Fe(CN)_6$, 0.1% Triton X-100 and 1 g/L X-gluc (5-bromo-4-chloro-3-indolyl-β-d-glucuronic acid). Seedlings were treated with successive ethanol solutions, with increasing ethanol concentrations, to gradually remove chlorophylls and other pigments, after which they were then visually inspected and photographed.

Quantitative real-time PCR analysis. Shoot or root RNAs were extracted from 2-month-old SAUR::iaaM, SbUGT::iaaM or wild-type tobacco plants using the RNeasy Plant Mini Kit including RNase-Free DNase set (Qiagen, Valencia, Calif.) according to the manufacturer's protocol. The iScript™ cDNA Synthesis Kit (Bio-Rad Laboratories, Richmond, Calif.) was used to synthesize cDNA, after which cDNA was used as a template for quantitative real-time PCR analysis using SsoFast™ EvaGreen® Supermix (Bio-Rad Laboratories, Richmond, Calif.) on a CFX96™ Real-Time PCR detection system (Bio-Rad Laboratories, Richmond, Calif.). Primer sequences for all genes analysed are as follows:

```
iaaM forward:
                                    (SEQ ID NO: 12)
5'-TGGATTTCTCCGAAGCACA-3';

iaaM reverse:
                                    (SEQ ID NO: 13)
5'-CCCGGTAACGCATTTCAT-3';

GH3 forward:
                                    (SEQ ID NO: 14)
5'-GGATTATGCAATTTCAAGG-3';

GH3 reverse:
                                    (SEQ ID NO: 15)
5'-ACGATGGGCTAAAGTGTCT-3';

EF1α forward:
                                    (SEQ ID NO: 16)
5'-GCTGCTCAGAAGAAGAAATG-3',
and EF1α reverse:
                                    (SEQ ID NO: 17)
5'-GAGCTGGTTCCAGACATACAC-3'.
```

The tobacco GH3 gene sequence was identified based on the deduced amino acid sequences from the *Arabidopsis* and soya bean GH3 gene sequences. EF1α was used to amplify cDNA of the internal reference gene, elongation factor 1a. Data were analysed using CFX Manager™ software version 2.0. The gene expression levels in each sample were normalized using the expression level of the elongation factor 1a gene in the same sample. Three biological replicates were performed with all treatments.

Evaluation of SbUGT::iaaM-39 rootstock in the glasshouse. The SbUGT::iaaM-39 and wild-type tobacco plants were vegetatively propagated and grew in glasshouse for one month before grafting. Scion and rootstock were jointed using the cleft graft technique (Lee and Oda, Horticul. Rev. 28:61-124 (2010)). Parafilm was used to wrap the graft union for at least one week. A total of 20 WT/WT and 10 WT/iaaM grafts were used for each experiment. Of the 20 WT/WT grafts, 10 were left with the lateral buds intact on the rootstock and the other 10 had the lateral buds manually removed from the rootstock. The growth of the grafted plants was recorded two months after grafting. Two months after grafting, apical portions of the scions were removed, and lateral bud release from scion shoots was recorded after 2 weeks.

Field evaluation of grafts. The SbUGT::iaaM-39 and wild-type tobacco plants were vegetatively propagated and grafted in the glasshouse, as described above. A total of 20 WT/WT grafts and 10 WT/iaaM-39 grafts were used for the experiment. Three weeks after grafting, all grafted plants were randomly planted in a field lot on the UConn depot campus in Storrs, Conn., USA. The 20 WT/WT grafts were divided into two groups: 10 with lateral buds on the rootstock intact and 10 with the rootstock lateral buds manually removed. Initial shoot heights of plants were recorded at time of transplanting in the field and then again at 60 and 90 days. All scions above the graft union were harvested at day 90. After removing leaves, scion shoot tissues were oven-dried at 70° C. for 10 days and then weighed. Shoot biomass was determined for each graft. Data were reported as means of all 10 replicates. Analysis of variance among field-grown graft combinations was performed using IBM SPSS 19.0 (IBM Corp., Somers, N.Y.). When sufficient differences (P<0.05) were observed, Fisher's protected least significant difference test (P=0.05) was performed to calculate differences between different treatments.

Crosses between SbUGT::iaaM-39 and SbUGT::CKX-64 plants and hybrid progeny evaluation. Wild-type, SbUGT::iaaM-39 and SbUGT::CKX-64 tobacco plants were vegetatively propagated. During flowering, wild-type pollen was used to pollinate wild-type, SbUGT::iaaM-39 or SbUGT::CKX-64 plants which had anthers removed before maturity to prevent undesired self-pollination. SbUGT::CKX-64 pollen was used to pollinate SbUGT::iaaM-39 flowers in the same way. Paper bags were used to wrap pollinated flowers, in order to reduce undesired pollination. The progeny seeds were germinated and grown on MS medium. Genomic DNA was extracted from leaves of seedlings using a modified CTAB method. The primer pairs, iaaM-F and iaaM-R or CKX-F and CKX-R, described above, were used to confirm the presence of the iaaM or CKX genes in hybrid plants, respectively. Eight days after germination, photographs and primary root length data were collected. Data were recorded on an average of 30 seedlings. Means between wild-type and transgenic plants were compared using the two-tailed Student's t-test with the pooled variance.

Root growth evaluation under glasshouse conditions. The SbUGT::iaaM-39, wild-type and one representative iaaM+CKX hybrid plant were vegetatively propagated and planted in pots with fritted clay medium in glasshouse. Ten days after planting, root number of each plant was recorded. Six weeks after rooting, shoot height of each plant was recorded. All plants were carefully dug out from medium. Root length was determined for each plant. Shoot and root tissues were oven-dried at 70° C. for 10 days and then weighed. Data were reported as means of all eight replicates. Means between wild-type and transgenic plants were compared using the two-tailed Student's t-test with the pooled variance.

Evaluation of iaaM+CKX hybrid rootstock in glasshouse. The SbUGT::iaaM-39, wild-type and one representative iaaM+CKX hybrid plant were used as rootstock, and wild-type scions were grafted, as described above. One group of WT/WT grafts has lateral buds intact on the rootstock, and the other group has the rootstock lateral buds manually removed. Three weeks after grafting, grafting success rates were recorded. Grafts with more than a 2-cm increase in scion's height growth were considered as successful grafts. For each rootstock/scion and lateral bud removal treatment, 8-11 grafts were performed as one replicate. Data were reported as means of three biological replicates. Analysis of variance on grafting success rates between different grafts was performed using IBM SPSS 19.0 (IBM Corp., Somers, N.Y.). When sufficient differences (P<0.05) were observed, Fisher's protected least significant difference test (P=0.05) was performed to calculate differences between groups.

Quantification of IAA and zeatin content. Hormone extractions were handled in the same manner as described (Krishnan and Merewitz, J. Plant Growth Regul. 34, 1-12 (2015); Krishnan et al., J. Am. Soc. Hortic. Sci. 141, 66-75 (2016)). About 50 mg frozen-dried root or shoot samples from two-month-old SbUGT::iaaM-39, SbUGT::CKX-64, one representative iaaM+CKX hybrid plant or wild-type samples was ground to a fine powder in liquid nitrogen using a mortar and pestle. IAA or zeatin content analysis was carried out using an ultra-high-performance LC-tandem mass spectrometer (UPLC/MS/MS) (Quattro Premier XE ACQUITY Tandem Quadrupole; Waters, Milford, Mass.). Samples from 10 plants were pooled for each replicate, and data were reported as a mean of three biological replicates. Analysis of variance was performed on IAA content data using IBM SPSS 19.0 (IBM Corp., Somers, N.Y.). When sufficient differences (P<0.05) were observed, Fisher's protected least significant difference test (P=0.05) was performed to calculate differences between groups. Means of zeatin content between SbUGT::CKX-64 and wild-type plants were compared using the two-tailed Student's t-test with the pooled variance.

Example 2

SbUGT::iaaM Expression Inhibited Outgrowth of Lateral Buds Following Decapitation The SbUGT::GUS fusion gene was predominantly active in roots of transgenic tobacco plants (FIG. 1A). The SbUGT promoter sequence was used to control the expression of the iaaM-coding sequence. Of 58 SbUGT::iaaM tobacco lines produced, more than 75% of these plants showed no difference in growth and developmental patterns in the aboveground organs when compared to wild-type plants (FIG. 1B). The remaining 25% showed a weak but visible auxin-overproducing phenotype characterized by slight downward-curled and epinastic leaves (FIG. 1C, SbUGT::iaaM-39 plant on the right). In contrast, the expression of the iaaM under the control of a small auxin up RNAs (SAUR) gene promoter, which is highly active in shoots and leaves, resulted in stunted shoot growth and strong leaf epinasity (FIG. 1D). Expression of iaaM in shoots appeared to inhibit lateral bud release in rootstocks following decapitation, as iaaM expression levels (FIG. 1E) positively correlated with lateral bud release delays of 6 weeks in SbUGT::iaaM-39, 4 weeks in SbUGT::iaaM-24 and 1 week in SbUGT::iaaM-15 lines.

In SbUGT::iaaM-39 transgenic plants, the iaaM gene was highly expressed in roots, but also detectable in shoot tissues (FIG. 1F). This result is slightly differently from histochemical staining of GUS activity in young seedlings (FIG. 1A), which suggests the activity of the SbUGT promoter could be developmentally regulated. In SbUGT::iaaM-39 roots, free IAA levels increased about threefold compared to wild type (Table 1), and expression of the endogenous auxin-responsive gene GRETCHEN HAGEN 3 (GH3) was increased (FIG. 1G). Free IAA level in SbUGT::iaaM-39 shoots also increased about twofold compared to that of wild-type plants, with 414.1 ng/g dry weight for SbUGT::iaaM-39 and 156.2 ng/g dry weight for wild-type plants. Based on these observations, the SbUGT::iaaM-39 line was selected for further experimentation.

TABLE 1

Endogenous auxin contents in roots of WT, SbUGT::iaaM-39 (iaaM), SbUGT::CKX-64 (CKX) and the SbUGT::iaaM-39/SbUGT::CKX-64 (iaaM + CKX) hybrid plants

| Plants | Root IAA content (ng/g DW) (mean ± SE) |
|---|---|
| Wild type | 351.9 ± 7.6c |
| iaaM | 946.4 ± 20.3a |
| CKX | 172.2 ± 15.8d |
| iaaM + CKX | 830.4 ± 33.4b |

Data represent the average of three biological replicates. Each replicate consists of the pooled root samples from 10 plants. Values followed by the different letters are significantly different at P<0.05 (ANOVA; LSD). SE, standard errors.

Example 3

Figure 3A:
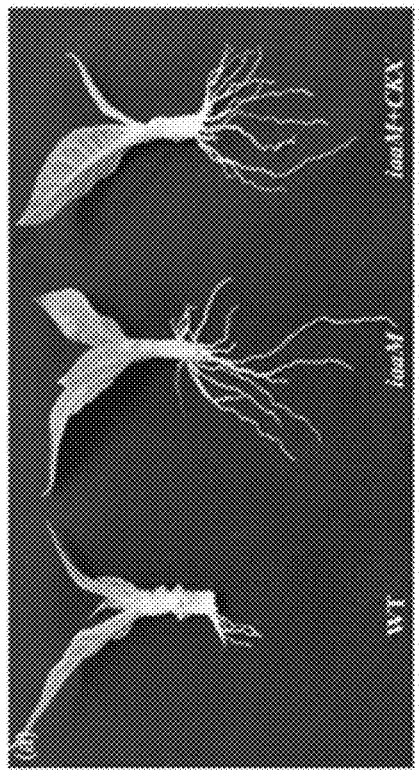
FIGS. 3A-3H show negative effects of the SbUGT::iaaM gene expression on root growth can be compensated with expression of the SbUGT::CKX gene.
Figures 3B, 3C, 3D:
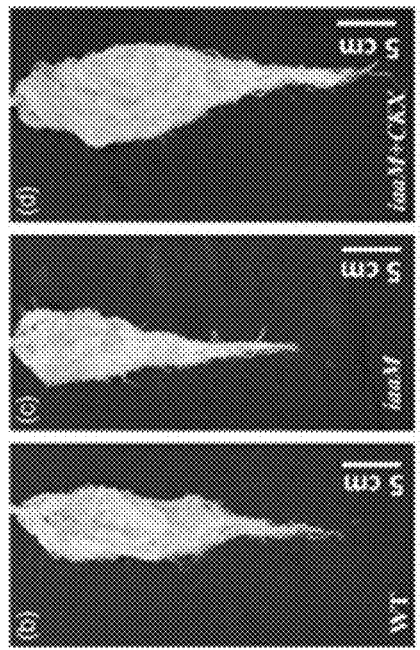
Figures 3E, 3F, 3G, 3H:
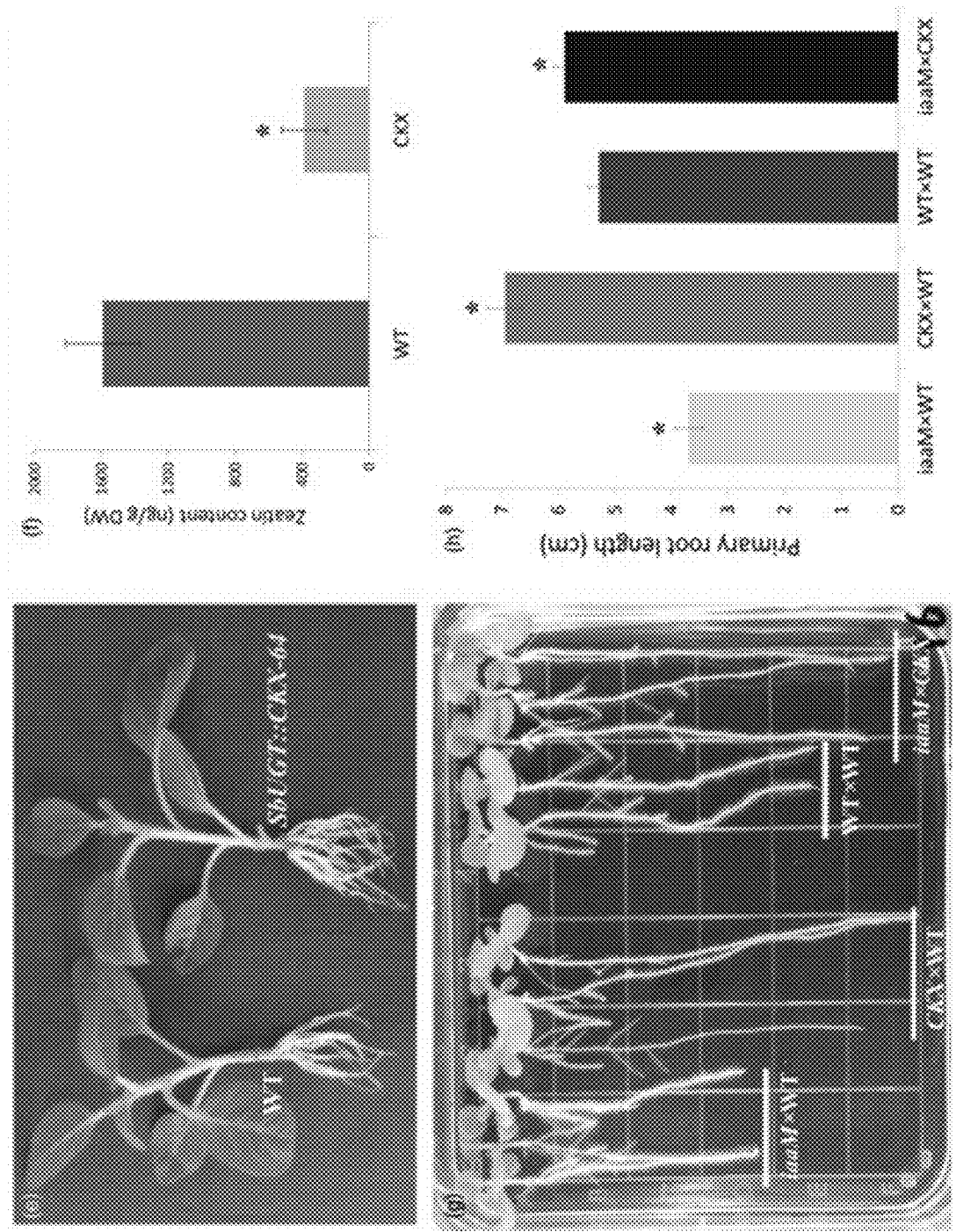
Figures 4A, 4B, 4C, 4D:
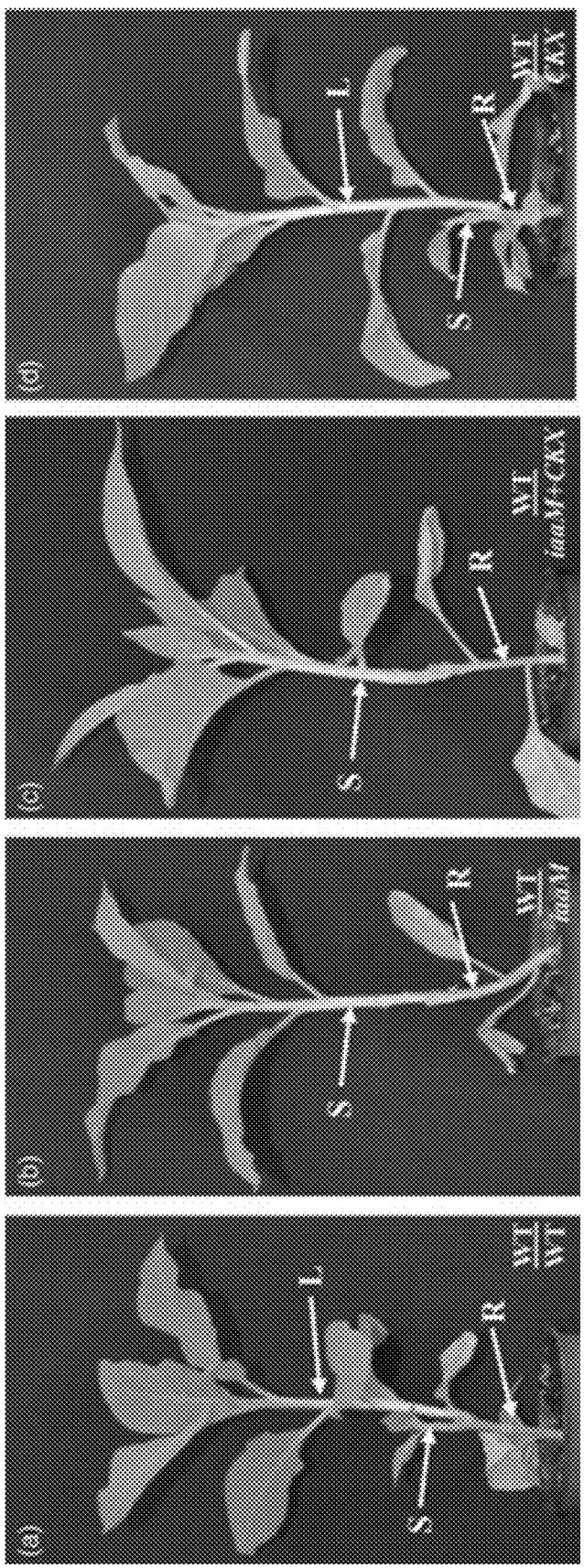
FIGS. 4A-4D show the SbUGT::iaaM-39/SbUGT::CKX-64 hybrid plant (iaaM+CKX) used as rootstock inhibited lateral bud release from their stumps and enhanced scion growth.

SbUGT::iaaM Gene Expression Suppressed Rootstock's Lateral Bud Release and Improved Grafting Success Rates After wild-type tobacco scions were grafted onto wild-type plant rootstocks (abbreviated as WT/WT), lateral shoots began to develop from the rootstock within 2 weeks of grafting and the growth of scions was reduced (FIG. 2A, 2 week after grafting, and FIG. 4A, 3 weeks after grafting). When lateral buds were removed from wild-type rootstock, vigorous scion growth was observed (FIG. 2B). However, no lateral bud release from the rootstocks of WT/SbUGT::iaaM-39 (abbreviated as WT/iaaM) grafts was observed, and scion growth was also vigorous (FIG. 2C). This was quite unlike scion growth of WT/WT grafts, which was vigorous only if the lateral buds of the rootstock were removed (FIG. 2D). These results demonstrate that under these conditions, there is no need to remove lateral buds from rootstock, thus eliminating costs associated with that procedure.

When WT plants were used as rootstock, a 24% grafting success rate was observed if lateral buds were not removed from the rootstock (Table 2). After manual removal of buds from the WT rootstock, the grafting success rate increased to 68%. On the other hand, when the iaaM plants were used as rootstocks under the identical experimental conditions, no lateral bud release was observed and the grafting success rate reached 91%, demonstrating that expression of the SbUGT::iaaM in rootstock significantly enhanced grafting success rates.

TABLE 2

Grafting success rates of grafts with or without removing lateral buds from rootstock stumps

| | Grafting success rates (mean ± SE) (%)[a] | | | |
|---|---|---|---|---|
| Grafting method | WT/WT (lateral buds intact on rootstock) | WT/WT (lateral buds removed from rootstock) | WT/iaaM (lateral buds intact on rootstock) | WT/iaaM + CKX (lateral buds intact on rootstock) |
| Decapitated plants as rootstock | 24 ± 4a | 68 ± 5b | 91 ± 1c | 89 ± 2c |

[a]Grafts with more than 2-cm increase in scion growth were considered as successful grafting. Data were collected 3 weeks after grafting. Each type of grafting has three replicates. For each replicate, 8-11 grafts were performed.
Values with the different letters are significantly different at P < 0.05 (ANOVA; LSD).
SE, standard errors.

Growth performance of WT/WT and WT/iaaM grafts were examined under field conditions (Table 3). While lateral bud release was observed from the rootstock of the WT/WT grafts 10 days after planting, no lateral buds were released from the rootstock of the WT/iaaM grafts, demonstrating that the use of iaaM rootstocks can eliminate the need for lateral buds removal under field conditions. With lateral buds removed from the rootstock of the WT/WT grafts, the scions grew more vigorously, as indicated by height and dry biomass, than the WT/WT grafts for which lateral buds were intact. Scion growth in the WT/iaaM grafts that exhibited no lateral bud release was similar to that of the WT/WT grafts after manual lateral bud removal from the rootstock. Finally, lateral bud release from the scions of the WT/iaaM grafts was similar to that of the WT/WT grafts following apical shoot excision (FIG. 2E), demonstrating that the iaaM rootstock had minimal effects on the branching behavior of scions.

TABLE 3

Growth performance of scions of field-grown grafts

| Grafts (scion/rootstock) | Height on day 60 (cm)$^a$ (mean ± SE) | Height on day 90 (cm)$^b$ (mean ± SE) | Dry scion biomass (g)$^c$ (mean ± SE) |
|---|---|---|---|
| WT/WT (lateral buds intact on rootstock) | 66.4 ± 1.7a | 99.8 ± 3.0a | 69.9 ± 2.0a |
| WT/WT (lateral buds removed from rootstock) | 76.3 ± 1.9b | 128.4 ± 3.1b | 83.8 ± 2.7b |
| WT/iaaM (lateral buds intact on rootstock) | 81.2 ± 3.3b | 127.8 ± 5.9b | 81.5 ± 3.2b |

$^a$Height on day 60: plant height after 60 days in the field.
$^b$Height on day 90: plant height after 90 days in the field.
$^c$Dry scion biomass includes all stem and branch biomass above the graft union (excluding leaves); data were collected after 90 days in the field.
Data were collected from 10 individual plants and presented as averages.
Values in the same column followed by the different letters are significantly different at p < 0.05 (ANOVA; LSD).
SE, standard errors.

Example 4

The Reduction in Root Growth Observed in SbUGT::iaaM Rootstock can be Compensated by SbUGT::CKX Expression One concern about application of the SbUGT::iaaM expression as a practical technology was an observed reduction in root growth. Although root initiation in iaaM cuttings was more rapid compared to that of the wild-type plants, root elongation and root biomass were reduced (FIGS. 3A-3C, Table 4). To circumvent the negative effects of iaaM gene expression on root growth, an *Arabidopsis* cytokinin oxidase/dehydrogenase gene (AtCKX2, abbreviated as CKX) was overexpressed in roots. In general, SbUGT::CKX tobacco plants displayed improved root elongation and increased root biomass. Although this phenomenon was observed in multiple CKX overexpression lines, one line, SbUGT::CKX-64 (FIG. 3E), was selected for further experiments. The roots of SbUGT::CKX-64 plants had significantly reduced endogenous cytokinin content compared to wild-type plants (FIG. 3F), demonstrating that expression of the SbUGT::CKX gene was effective at reducing cytokinin levels in roots.

TABLE 4

Growth characteristics of stem cuttings of SbUGT::iaaM-39 (iaaM) and SbUGT::iaaM-39/SbUGT::CKX-64 (iaaM + CKX) plants under glasshouse conditions

| Plants | Root number (mean ± SE)$^a$ | Root length (cm) (mean ± SE)$^b$ | Dry root biomass (mg) (mean ± SE)$^b$ | Shoot height (cm) (mean ± SE)$^b$ | Dry shoot biomass (mg) (mean ± SE)$^b$ |
|---|---|---|---|---|---|
| WT | 4.4 ± 0.5 | 28.2 ± 0.7 | 543.6 ± 14.6 | 48.0 ± 0.9 | 3093.4 ± 146.1 |
| iaaM | 13.8 ± 1.1* | 24.5 ± 0.9* | 345.3 ± 23.9* | 46.7 ± 1.5 | 2969.5 ± 73.25 |
| iaaM + CKX | 14.4 ± 1.2* | 33.7 ± 1.0* | 688.3 ± 57.3* | 47.5 ± 1.2 | 3157.7 ± 55.3 |

$^a$The average number of emerged roots per stem after being rooted in fritted clay medium for 10 days.
$^b$Data were collected after being rooted in fritted clay medium for 6 weeks.
Data were collected from eight replicates and presented as averages.
Asterisks represent significant differences compared to wild type using two-tailed Student's t-test with the pooled variance (P < 0.05).
Bars represent standard errors.

Crosses of SbUGT::iaaM-39 with SbUGT::CKX-64 produced hybrids (iaaM+CKX) with both the iaaM and CKX transgenes present in progeny plants. Analysis of IAA content in root tissue of plants from both the SbUGT::iaaM-39 and iaaM+CKX hybrid transgenic lines showed that overexpression of the iaaM gene led to significant increases in auxin concentration but overexpression of the CKX gene reduced auxin concentrations with or without overexpression of the iaaM gene (Table 1). These results demonstrate that expression of the SbUGT::CKX gene results in reduced IAA content in roots.

The SbUGT::CKX overexpression-mediated reduction in root auxin content may contribute to the improvement in root elongation and root biomass in iaaM+CKX hybrid plants.

Improvement of root elongation was observed in the seedlings derived from iaaM+CKX hybrid seed (FIGS. 3G, 3H). Rooting of shoot cuttings from iaaM+CKX hybrid plants after 10 days was also improved compared to wild-type plants (FIG. 3A). Six weeks after rooting, the iaaM+CKX hybrid plants produced longer roots than both SbUGT::iaaM-39 and wild-type plants (FIGS. 3B-3D). Dry root biomasses of the iaaM+CKX hybrid progeny plants were significantly greater compared to those of wild-type plants. Shoot heights and dry shoot biomasses were similar between the iaaM+CKX and wild-type plants (Table 4). These results demonstrate that reducing cytokinin levels in roots can neutralize the negative effects of root length and root biomass caused by the iaaM gene expression, and act synergistically with auxin to promote root initiation.

Example 5

Simultaneous Expression of SbUGT::iaaM and SbUGT::CKX Genes Suppressed Lateral Bud Release from Rootstock and Improved Grafting Success Rates Three weeks after wild-type scions were grafted on to wild-type, SbUGT::iaaM-39, SbUGT::CKX-64 and SbUGT::iaaM+SbUGT::CKX rootstock, respectively, WT/WT grafts (FIG. 4A) had little scion growth because of outgrowth of a lateral shoot; WT/iaaM (FIG. 4B) and WT/iaaM+CKX (FIG. 4C) had no lateral buds released from their rootstock stumps and showed vigorous scion growth; and WT/CKX (FIG. 4D) had lateral shoot outgrowth with little scion growth. Lateral buds were released from both the wild-type rootstock (FIG. 4A) and the CKX rootstock (FIG. 4D), but not from the iaaM or the iaaM+CKX rootstock (FIGS. 4B and 4C). When lateral buds were released from the wild-type or CKX rootstock, scion growth was inhibited (FIGS. 4A and 4D) but scion growth was vigorous when grafted onto the iaaM or the iaaM+CKX hybrid rootstock (FIGS. 4B and 4C). Grafting success rates were determined when iaaM+CKX hybrid plants were used as rootstock. Similar to that of the iaaM-overexpressing rootstock, grafting success rate was dramatically improved when iaaM+CKX hybrid was used as rootstock relative to grafting success rate observed with wild-type rootstock (Table 2). These results demonstrate that expression of both the SbUGT::iaaM and SbUGT::CKX genes in rootstock plants repressed lateral bud release from the rootstock and improved grafting success rate, similar to the effects of SbUGT::iaaM gene.

Figure 5A:
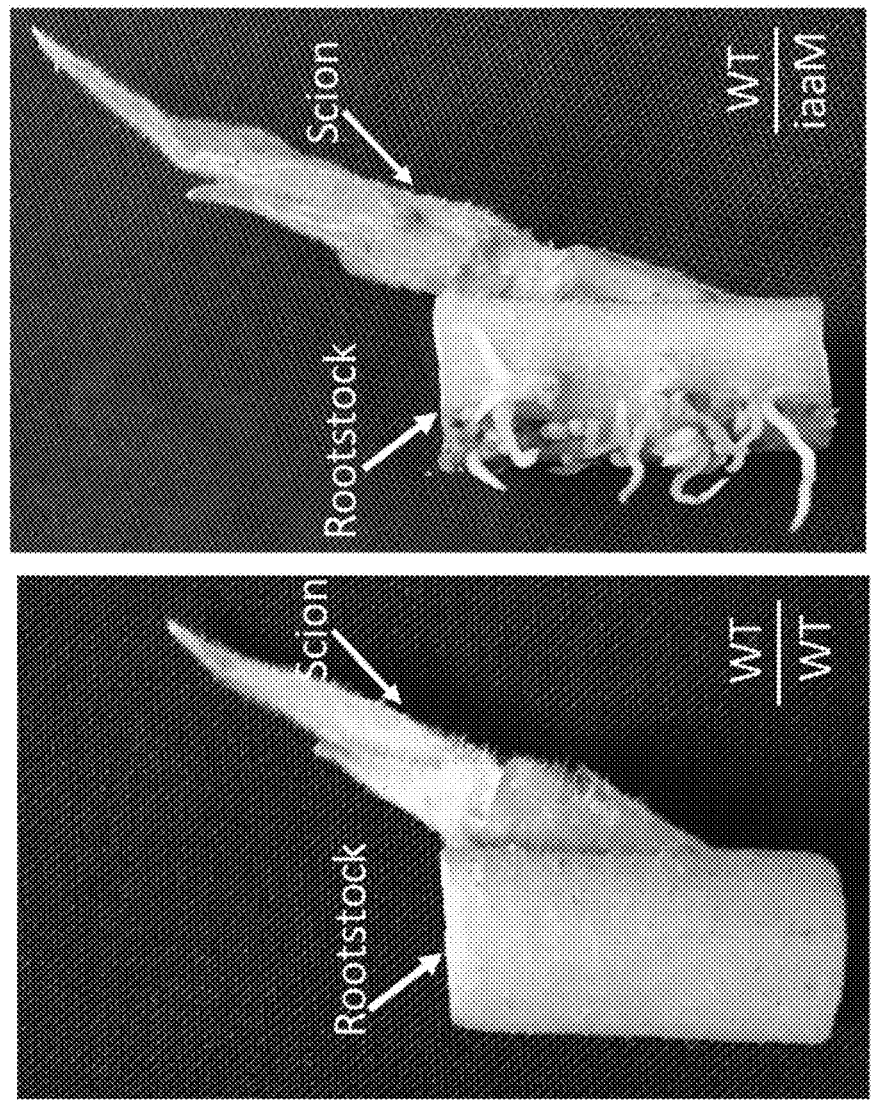
FIGS. 5A and 5B show over-expression of the iaaM gene in rootstock enhances graft union formation between the scion and rootstock.
Figure 5B:
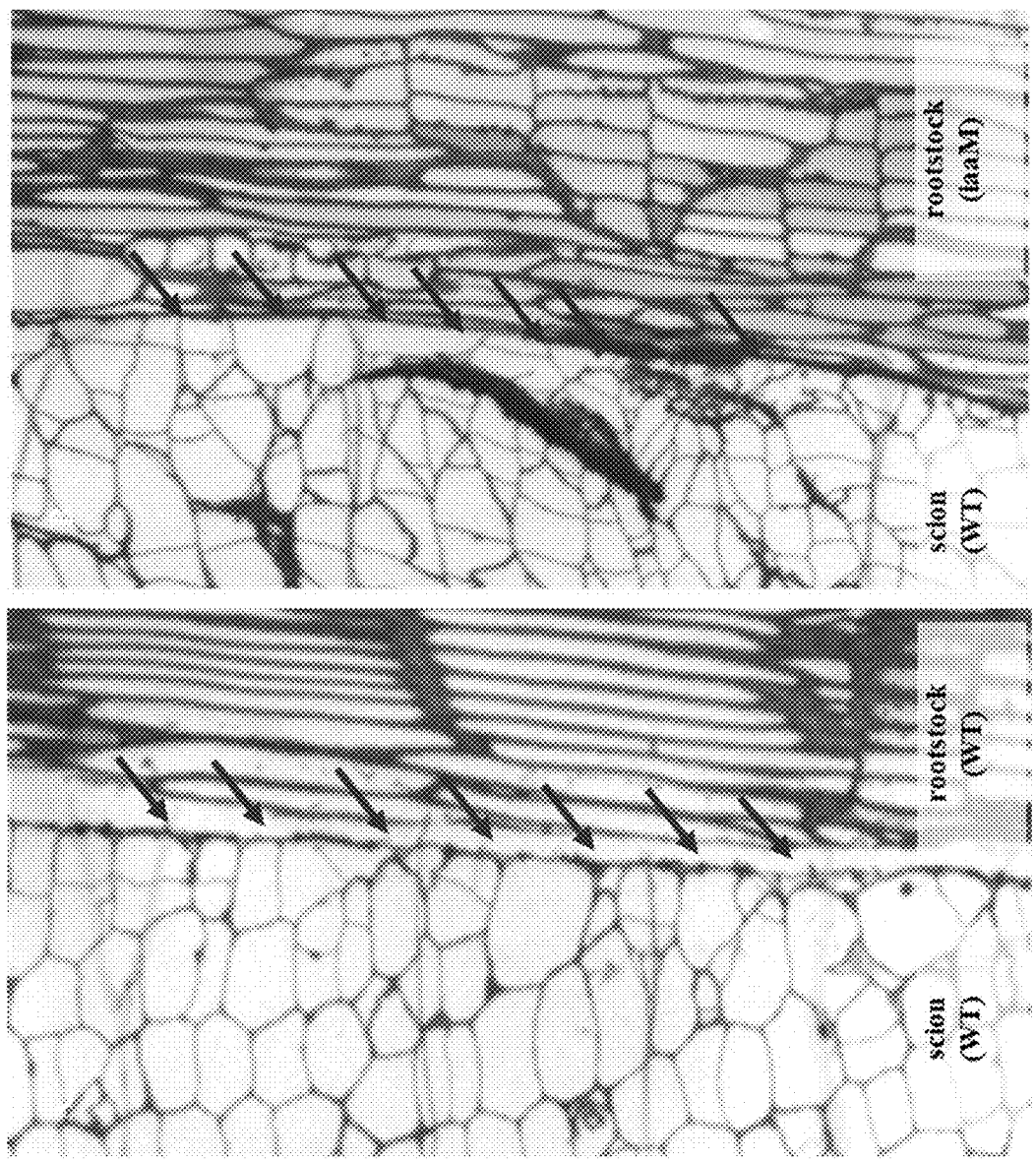

FIGS. 5A and 5B show that over-expression of the iaaM gene in rootstock enhances graft union formation between the scion and rootstock. FIG. 5A shows a graft union between a wild-type (WT) scion and a WT rootstock (left panel) and a graft union between a WT scion and iaaM rootstock (right panel). FIG. 5B shows the junctions between scions and rootstocks (see arrows) in the graft union between a WT scion and a WT rootstock (left panel) and graft union between a WT scion and iaaM rootstock (right panel). The graft union between a WT scion and a WT rootstock was poorly formed while the union was well formed between a WT scion and the iaaM rootstock.

Figure 6:
FIG. 6 shows a graft union between a WT scion and a WT rootstock (left) and WT scion and an iaaM rootstock (right).

FIG. 6 shows a graft union between a WT scion and a WT rootstock (left) and WT scion and a iaaM rootstock (right). Well-formed graft union was observed between a WT scion and the iaaM rootstock (WT/SbUGT::iaaM). In the WT/WT, the split is getting deeper as time passes.

Figure 7:
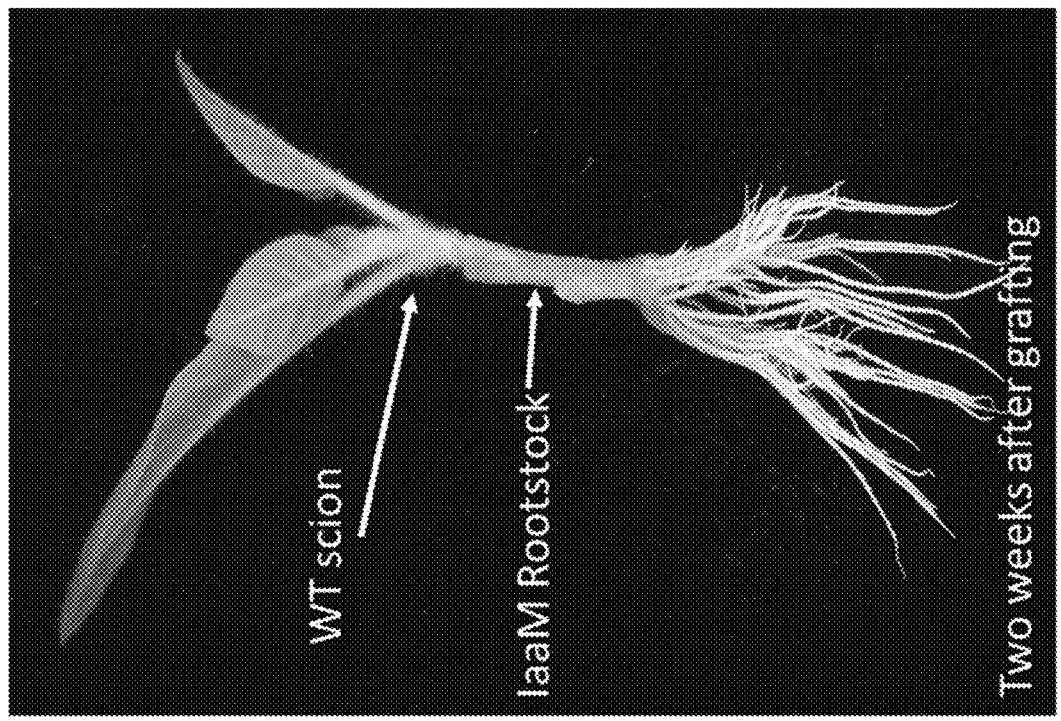
FIG. 7 shows a WT/WT plant one month after grafting and a WT/SbUGT::iaaM plant two weeks after grafting.
Figure 7:
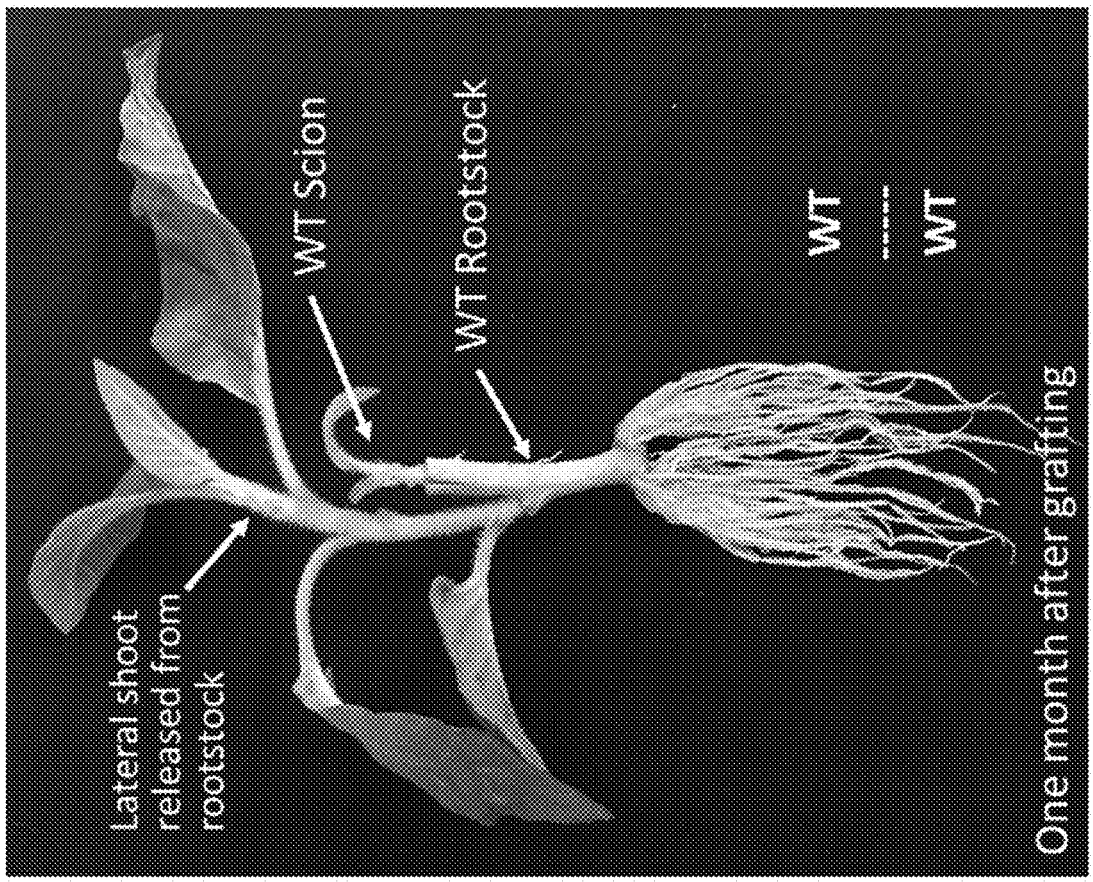

FIG. 7 shows a WT/WT plant one month after grafting and a WT/SbUGT:iaaM plant two weeks after grafting. Lateral shoots were released from WT rootstock and thus inhibited scion growth. However, no lateral shoots were released from the SbUGT::iaaM rootstock and the scion grafted on the iaaM rootstock exhibited good growth.

Figure 8:
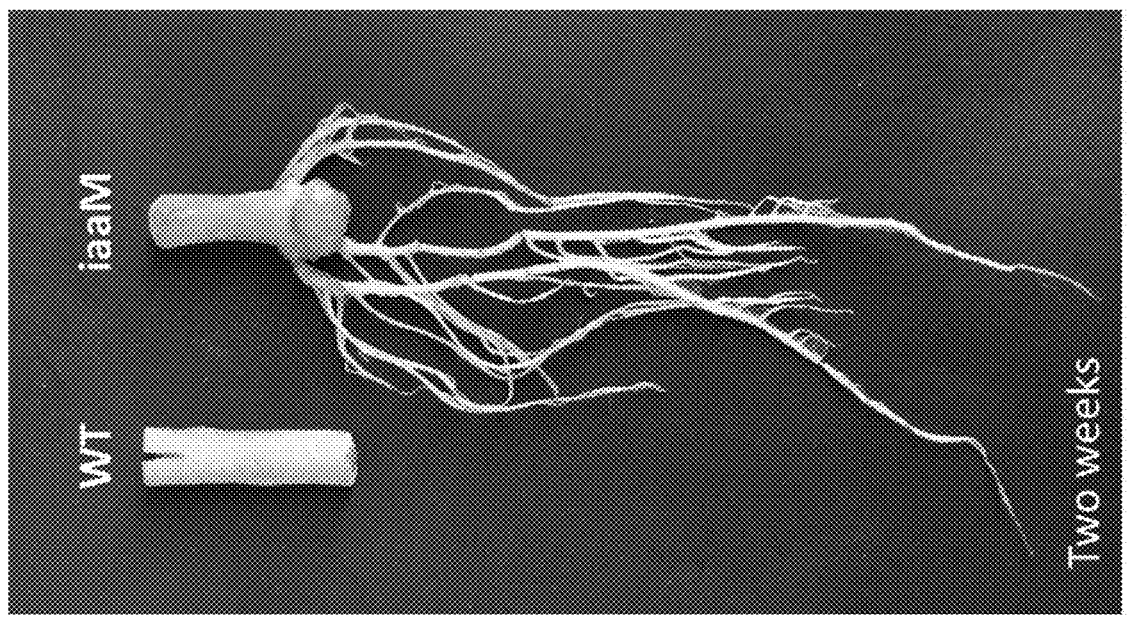
FIG. 8 shows stem sections of WT/WT plant and WT/SbUGT:iaaM plant.

FIG. 8 shows stem sections of WT/WT plant and WT/SbUGT::iaaM plant. SbUGT::iaaM stem section: The cut was healed after two weeks and good root can be produced. WT stem section: The cut was not healed and no root was produced.

Example 6

Discussion

This study demonstrates that root-predominant expression of an iaaM gene, whose product catalyses biosynthesis of an auxin precursor, results in a series of improved rootstock characteristics. However, root elongation and root biomass of iaaM rootstock were adversely affected compared to those of the wild-type rootstock. Overexpression of a cytokinin degradation gene (CKX) compensated the negative effect of the iaaM gene expression on root elongation and biomass of rootstocks. The results have demonstrated that increases in auxin level and reductions in cytokinin concentration predominantly in roots can produce several beneficial characteristics including inhibited lateral bud release from the rootstock, improved grafting success rates and enhanced root initiation and root biomass. This technology may also be useful in other woody plants, such as apple and pear, for improving the quality of rootstock because effects of auxin and cytokinin on plant growth and development are basically the same in higher plants.

Using rootstocks that overexpress the SbUGT::iaaM gene, the WT/iaaM grafts had a much higher grafting success rate (91%) than the WT/WT grafts on which lateral buds were manually removed (68%). These results provide additional evidences that auxin plays a critical role in grafting success.

Fast initiation and establishment of adventitious roots from shoot cuttings are important traits for rootstock plants. However, many plant species or cultivars having a number of excellent rootstock characteristics are difficult to root. Dwarf apple rootstock varieties that have been commonly used for grafting are difficult to root from shoot cuttings The RolB gene from *A. rhizogenes* has been used to enhance rooting of dwarf apple and pear varieties. The disclosed auxin-overproducing transgenic rootstock lines displayed similar enhanced rooting ability but also showed inhibition of lateral buds outgrowth from rootstock and improved grafting success rates that were not reported with the use of RolB transgenic rootstock.

Analyses for plant hormone concentrations in SbUGT::iaaM and SbUGT::CKX transgenic plants revealed that overexpression of the CKX gene resulted in reduced auxin levels. The lower auxin levels may have contributed to the improvement in root growth that was observed in the CKX-overexpressing rootstock.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clause:

Clause 1. A method of producing rootstock plants, the method comprising:
Obtaining a first transgenic plant overexpressing a gene for auxin production in the roots;
Obtaining a second transgenic plant overexpressing a gene for cytokinin degradation in the roots; and,
Producing crosses between the first transgenic plant and the second transgenic plant to obtain rootstock plants.

Clause 2. The method of clause 1, wherein the first transgenic plant comprises a root-predominant promoter operably linked to the gene for auxin production.

Clause 3. The method of clause 1, wherein the second transgenic plant comprises a root-predominant promoter operably linked to the gene for cytokinin degradation.

Clause 4. The methods of clauses 1 to 3 further comprising selecting plants with enhanced grafting traits.

Clause 5. The methods of clauses 1 to 3 further comprising selecting plants with enhanced rooting capacity.

Clause 6. The methods of clauses 1 to 5, wherein the gene for auxin production is an iaaM gene.

Clause 7. The methods of clause 6, wherein the iaaM gene is a heterologous gene.

Clause 8. The methods of clauses 1 to 5, wherein the gene for cytokinin degradation is a CKX gene.

Clause 9. The methods of clause 8, wherein the CKX gene is a heterologous gene.

Clause 10. The methods of clauses 1 to 5, wherein the root-predominant promoter is a SbUGT promoter.

Clause 11. The methods of clause 10, wherein the root-predominant promoter is a heterologous promoter.

Clause 12. A rootstock plant produced by the methods of any of clauses 1 to 11.

Clause 13. The rootstock plant of clause 12, wherein the plant has enhanced grafting traits.

Clause 14. The rootstock plant of clause 12, wherein the plant has enhanced rooting capacity.

Clause 15. The rootstock plant of any of clauses 12 to 14, wherein the plant is selected from the group comprising fruit and nut trees such as apple, peach, plum, pear, citrus, cherry, hazelnut, and filbert; grape vines; woody shrubs such as roses and camellias; trees such as ash, beech, birch, cedar, ornamental cherry, dogwood, fir, honey locust, maple, redbud, spruce and witch hazel.

Clause 16. A transgenic rootstock plant comprising a first isolated nucleic acid encoding an auxin synthesis-related gene and/or a second isolated nucleic acid encoding a cytokinin degradation-related gene, wherein the first isolated nucleic acid is operably linked to a heterologous root-specific promoter and the second isolated nucleic acid is operably linked to a heterologous root-specific promoter.

Clause 17. The transgenic rootstock plant of clause 16, wherein the transgenic rootstock plant comprises a first isolated nucleic acid encoding an auxin synthesis-related gene or a second isolated nucleic acid encoding a cytokinin degradation-related gene.

Clause 18. The transgenic rootstock plant of clause 16, wherein the transgenic rootstock plant comprises a first isolated nucleic acid encoding an auxin synthesis-related gene and a second isolated nucleic acid encoding a cytokinin degradation-related gene.

Clause 19. The transgenic rootstock plant of any one of clauses 16-18, wherein the auxin synthesis-related gene is an iaaM gene.

Clause 20. The transgenic rootstock plant of clause 19, wherein the iaaM gene comprises a polynucleotide sequence of SEQ ID NO: 2.

Clause 21. The transgenic rootstock plant of any one of clauses 16-20, wherein the cytokinin degradation-related gene is a CKX gene.

Clause 22. The transgenic rootstock plant of clause 21, wherein the CKX gene comprises a polynucleotide sequence of SEQ ID NO: 4.

Clause 23. The transgenic rootstock plant of any one of clauses 16-22, wherein the heterologous root-specific promoter is a SbUGT promoter.

Clause 24. The transgenic rootstock plant of clause 23, wherein the SbUGT promoter comprises a polynucleotide sequence of SEQ ID NO: 1.

Clause 25. The transgenic rootstock plant of any one of clauses 16-24, wherein the transgenic rootstock plant has enhanced grafting traits and/or enhanced rooting capacity as compared to a control plant.

Clause 26. A method of producing a transgenic rootstock plant having enhanced grafting traits and/or enhanced rooting capacity, the method comprising: a) introducing into a plant a first isolated nucleic acid encoding an auxin synthesis-related gene, wherein the first isolated nucleic acid is operably linked to a heterologous root-specific promoter, and/or a second isolated nucleic acid encoding an cytokinin degradation-related gene, wherein the second isolated nucleic acid is operably linked to a heterologous root-specific promoter; and b) regenerating the transformed plant cell to produce a rootstock plant.

Clause 27. A method of producing a transgenic rootstock plant having enhanced grafting traits and/or enhanced rooting capacity, the method comprising: a) obtaining a first transgenic plant comprising a first isolated nucleic acid encoding an auxin synthesis-related gene, wherein the first isolated nucleic acid is operably linked to a heterologous root-specific promoter; b) obtaining a second transgenic plant comprising a second isolated nucleic acid encoding an cytokinin degradation-related gene, wherein the second isolated nucleic acid is operably linked to a heterologous root-specific promoter; and c) generating a cross between the first transgenic plant and the second transgenic plant thereby producing the transgenic rootstock plant.

Clause 28. The method of clause 26 or 27, wherein the transgenic rootstock plant has enhanced grafting traits and/or enhanced rooting capacity compared to a control plant.

Clause 29. The method of any one of clauses 26-28, wherein the auxin synthesis-related gene is an iaaM gene.

Clause 30. The method of clause 29, wherein the iaaM gene comprises a polynucleotide sequence of SEQ ID NO: 2.

Clause 31. The method of any one of clauses 26-30, wherein the cytokinin degradation-related gene is a CKX gene.

Clause 32. The method of clause 31, wherein the CKX gene comprises a polynucleotide sequence of SEQ ID NO: 4.

Clause 33. The method of any one of clauses 26-32, wherein the root-specific promoter is a SbUGT promoter.

Clause 34. The method of clause 33, wherein the SbUGT promoter comprises a polynucleotide sequence of SEQ ID NO: 1.

Clause 35. A transgenic rootstock plant produced by the method of any of clauses 26 to 34.

Clause 36. The transgenic rootstock plant of any one of clauses 24, 25, or 35, wherein the plant is a fruit tree, a nut tree, a woody shrub, a hardwood tree, a softwood tree, a crop plant, or an ornamental plant.

Clause 37. The transgenic rootstock plant of any one of clauses 24, 25, or 35, wherein the plant is a tree.

Clause 38. The transgenic rootstock plant of clause 36 or 37, wherein the tree is a citrus tree.

Clause 39. A method of producing a grafted plant, the method comprising contacting the transgenic rootstock plant of any one of clauses 35-38 with a scion.

Appendix

```
SbUGT promoter (SEQ ID NO: 1)
Ctagaagaccagataaacgatacgtaagcaagtacgtcatcaaataagct
tctcctctctctgtttctataattatatattagtcgagacttcattgagc
aaaatcctatattgcatcctttctcatgcaggccaccataaatattccat
tccaagaattccaaatttgcaaatatacacataattaa iaaM (nt) (SEQ ID NO: 2)
atgtcagcttcacctctccttgataaccagtgcgatcatctcccaaccaa
aatggtggatctgacaatggtcgataaggcggatgaattggaccgcaggg
tttccgatgccttcttagaacgagaagcttctaggggaaggaggattact
caaatctccaccgagtgcagcgctgggttagcttgcaaaaggctggccga
tggtcgcttccccgagatctcagctggtggaaaggtagcagttctctccg
cttatatctatattggcaaagaaattctggggcggatacttgaatcgaaa
ccttgggcgcgggcaacagtgagtggtctcgttgccatcgacttggcacc
attttgcatggatttctccgaagcacaactaatccaagccctgttttgc
tgagcggtaaaagatgtgcaccgattgatcttagtcatttcgttggccatt
tcaatctctaagactgccggctttcgaaccctgccaatgccgctgtacga
gaatggcacgatgaaatgcgttaccgggtttaccataaccctgaagggg
ccgtgccatttgacatggtagcttatggtcgaaacctgatgctgaaggt
tcggcaggttcctttccaacaatcgacttgctctacgactacagaccgtt
ttttgaccaatgttccgatagtggacggatcggcttccttccggaggatg
ttcctaagccgaaagtggcggtcattggcgctggcattccggactcgtg
gtggcaaacgaactgcttcatgctgggtagacgatgttacaatatatga
agcaagtgatcgtgttggaggcaagctttggtcacatgctttcaggcgca
ctccagtgtcgtggccgaaatggggcgatgcgattctctcctgctgca
ttctgcttgttttcttcctcgagcgttacggcctgtcttcgatgaggcc
gttcccaaatcccgcacagtcgacacttacttggtctaccaaggcgtcc
aatacatgtggaaagccgggcagctgccaccgaagctgttccatcgcgtt
tacaacggttggcgtgcgttcttgaaggacggttttcatgagcgagatat
tgtgttggcttcgcctgtcgctattactcaggccttgaaatcaggagaca
ttaggtgggctcatgactcctggcaaatttggctgaaccgtttcgggagg
gagtcctctcttcagggatagagaggatctttctgggcacacatctcc
tggtggtgaaacatggagttttcctcatgattgggacctattcaagctaa
tgggaataggatctgcgggtttggtccagttttgaaagcgggtttatt
gagatcctccgcttggtcatcaacggatatgaagaaaatcagcggatgtg
ccctgaaggaatctcagaacttccacgtcggatcgcatctgaagtggtta
acggtgtctgtgagccagcgcatatgccatgttcaagtcaggggcgatt
cagaaggaaaagacaaaaataaagataaggcttaagagcgggatatctga
actttatgataaggtggtggtcacatctgactcgcaaatatccaactca
ggcattgcctgacatgcgataccatatttttcaggcaccagtgaaccaa
gcggttgataacagccatatgacaggatcgtcaaaactcttcctgatgac
tgaacgaaaattctggttagaccatatcctcccgtcttgtgtcctcatgg
acgggatcgcaaaagcagtgtattgcctggactatgagtcgcaggatccg
aatgctaaaggtctagtgctcatcagttatacatgggaggacgactccca
caagctgttggcggtccccgacaaaaaagagcgattatgtctgctgcggtg
acgcaatttcgagatctttcccggcgtttgcccagcacctattttcctgcc
tgcgctgattacgaccaaaatgttattcaacatgattggcttacagacga
gaatgccgggagctttcaaactcaaccggcgtggtgaggattttat
ctgaagaactttctcttcaagcactggacacggctaatgataccggagtt
tacttggcgggttgcagttgttccttcacaggtggatgggtggagggtgc
tattcagaccgcgtgtaacgcgtctgtgcaattatccacaattgtggag
gcattttggcaaagggcaatcctctcgaacactcttggaagagatataac
taccgcactagaaattag iaaM (aa) (SEQ ID NO: 3)
MSASPLLDNQCDHLPTKMVDLTMVDKADELDRRVSDAFLEREASRGRRIT
QISTECSAGLACKRLADGRFPEISAGGKVAVLSAYIYIGKEILGRILESK
PWARATVSGLVAIDLAPFCMDFSEAQLIQALFLLSGKRCAPIDLSHFVAI
SISKTAGFRTLPMPLYENGTMKCVTGFTITLEGAVPFDMVAYGRNLMLKG
SAGSFPTIDLLYDYRPFFDQCSDSGRIGFFPEDVPKPKVAVIGAGISGLV
VANELLHAGVDDVTIYEASDRVGGKLWSHAFRDAPSVVAEMGAMRFPPAA
FCLFFFLERYGLSSMRPFPNPGTVDTYLVYQGVQYMWKAGQLPPKLFHRV
YNGWRAFLKDGFHERDIVLASPVAITQALKSGDIRWAHDSWQIWLNRFGR
ESFSSGIERIFLGTHPPGGETWSFPHDWDLFKLMGIGSSGFGPVFESGFI
EILRLVINGYEENQRMCPEGISELPRRIASEVVNGVSVSQRICHVQVRAI
QKEKTKIKIRLKSGISELYDKVVVTSGLANIQLRHCLICDINIFQAPVNQ
AVDNSHMTGSSKLFLMTERKFWLDHILPSCVLMDGIAKAVYCLDYESQDP
NGKGLVLISYTWEDDSHKLLAVPDKKERLCLLRDAISRSFPAFAQHLFPA
CADYDQNVIQHDWLTDENAGGAFKLNRRGEDFYSEELFFQALDTANDTGV
YLAGCSCSFTGGWVEGAIQTACNAVCAIIHNCGGILAKGNPLEHSWKRYN
YRTRN CKX2 (nt) (SEQ ID NO: 4)
atggctaatcttcgtttaatgatcactttaatcacggttttaatgatcac
caaatcatcaaacggtattaaaattgatttacctaaatcccttaacctca
ccctctctaccgatccttccatcatctccgcagcctctcatgacttcgga
aacataaccaccgtgaccccccggcggcgtaatctgcccctcctccaccgc
tgatatctctcgtctcctccaatacgccgcaaacggaaaaagtacattcc
aagtagcggctcgtggccaaggccactccttaaacggccaagcctcggtc
tccggcggagtaatcgtcaacatgacgtgtatcactgacgtggtggttc
aaaagacaagaagtacgctgacgtggcggccgggacgttatgggtggatg
tgcttaagaagacggcggagaaaggggtgtcgccggtttcttggacggat
tatttgcatataaccgtcggaggaacgttgtcgaatggtggaattggtgg
tcaagtgtttcgaaacggtcctcttgttagtaacgtccttgaattggacg
ttattactgggaaaggtgaaatgttgacatgctcgcgacagtcaaaccca
gaattgttctatggagtgttaggaggtttgggtcaatttggaattataac
gagagccagaattgttttggaccatgcacctaaacgggccaaatggttto
ggatgctctacagtgatttcacaactttttacaaaggaccaagaacgttg
atatcaatggcaaacgatattggagtcgactatttagaaggtcaaatatt
tctatcaaacggtgtcgttgacacctcttttttcccaccttcagatcaat
ctaaagtcgctgatctagtcaagcaacacggtatcatctatgttcttgaa
gtagccaagtattatgatgatcccaatctcccatcatcagcaaggttat
tgacacattaacgaaaacattaagttacttgcccgggttcatatcaatgc
acgacgtggcctacttcgatttcttgaaccgtgtacatgtcgaagaaaat
aaactcagatcttttgggattatgggaacttcctcatccttggcttaacct
ctacgttcctaaatctcggattctcgattttcataacggtgttgtcaaag
acattcttcttaagcaaaaatcagcttcgggactcgctcttctctatcca
acaaaccggaataaatgggacaatcgtatgtcggcgatgataccagagat
cgatgaagatgttatatatattatcggactactacaatccgctacccaa
aggatcttccagaagtggagagcgttaacgagaagataattaggttttgc
aaggattcaggtattaagattaagcaatatctaatgcattatactagtaa
agaagattggattgagcattttggatcaaaatgggatgattttcgaaga
ggaaagatctatttgatcccaagaaactgttatctccagggcaagcatc
ttttga CKX2 (aa) (SEQ ID NO: 5)
MANLRLMIILITVLMITKSSNGIKIDLPKSLNLTLSTDPSIISAASHDFG
NITIVTPGGVICPSSTADISRLLQYAANGKSTFQVAARGQGHSLNGQASV
SGGVIVNMTCITDVVVSKDKKYADVAAGTLWVDVLKKTAEKGVSPVSWTD
YLHITVGGTLSNGGIGGQVFRNGPLVSNVLELDVITGKGEMLTCSRQLNP
ELFYGVLGGLGQFGIITRARIVLDHAPKRAKWFRMLYSDPTTFTKDQERL
ISMANDIGVDYLEGQIFLSNGVVDTSFFPPSDQSKVADLVKQHGIIYVLE
VAKYYDDPNLPIISKVIDILTKILSYLPGFISMHDVAYFDFLNRVHVEEN
KLRSLGLWELPHPWLNLYVPKSRILDFHNGVVKDILLKQKSASGLALLYP
TNRNKWDNRMSAMIPEIDEDVIYIIGLLQSATPKDLPEVESVNEKIIRFC
KDSGIKIKQYLMHYTSKEDWIEHFGSKWDDFSKRKDLFDPKKLLSPGQDI
F SbUGT::iaaM (nt) (SEQ ID NO: 6)
ctagaagaccagataaacgatacgtaagcaagtacgtcatcaaataagct
tctcctctctctgtttctataattatatattagtcgagacttcattgagc
aaaatcctatattgcatcctttctcatgcaggccaccataaatattccat
tccaagaattccaaatttgcaaatatacacataattaaatgtcagcttca
cctctccttgataaccagtgcgatcatctcccaaccaaaatggtggatct
gacaatggtcgataaggcggatgaattggaccgcagggtttccgatgcct
tcttagaacgagaagcttctaggggaaggaggattactcaaatctccacc
gagtgcagcgctgggttagcttgcaaaaggctggccgatggtcgcttccc
cgagatctcagctggtggaaaggtagcagttctctccgcttatatctata
ttggcaaagaaattctggggcggatacttgaatcgaaaccttgggcgcgg
```

Appendix-continued gcaacagtgagtggtctcgttgccatcgacttggcaccattttgcatgga
tttctccgaagcacaactaatccaagccctgtttttgctgagcggtaaaa
gatgtgcaccgattgatcttagtcatttcgtggccatttcaatctctaag
actgccggctttcgaaccctgccaatgccgctgtacgagaatggcacgat
gaaatgcgttaccgggtttaccataaccctttgaagggcccgtgccatttg
acatggtagcttatggtcgaaacctgatgctgaagggttcggcaggttcc
tttccaacaatcgacttgctctacgactacagaccgtttttttgaccaatg
ttccgatagtggacggatcggcttctttccggaggatgttcctaagccga
aagtggcggtcattggcgctggcatttccggactcgtggtggcaaacgaa
ctgcttcatgctggggtagacgatgttacaatatatgaagcaagtgatcg
tgttggaggcaagcttttggtcacatgctttcagggacgctcctagtgtcg
tggccgaaatgggggcgatgcgattcctcctgctgcattctgcttgttt
ttcttcctcgagcgttacggcctgtcttcgatgaggccgttcccaaatcc
cggcacagtcgacacttacttggtctaccaaggcgtccaatacatgtgga
aagcgggcagctgccaccgaagctgttccatcgcgtttacaacggttgg
cgtgcgttcttgaaggacggttttcatgagcgagatattgtgttggcttc
gcctgtcgctattactcaggccttgaaatcaggagacattaggtgggctc
atgactcctggcaaatttggctgaaccgtttcgggagggagtccttctct
tcagggatagagaggatctttctgggcacacatcctcctggtggtgaaac
atggagttttcctcatgattgggacctattcaagctaatgggaataggat
ctggcgggtttggtccagttttttgaaagcgggtttattgagatcctccgc
ttggtcatcaacggatatgaagaaaatcagcggatgtgccctgaaggaat
ctcagaacttccacgtcggatcgcatctgaagtggttaacggtgtgtctg
tgagccagcgcatatgccatgttcaagtcagggcgattcagaaggaaaag
acaaaaataaagataaggcttaagagcgggatatctgaactttatgataa
ggtggtggtcacatctggactcgcaaatatccaactcaggcattgcctga
catgcgataccaatattttcaggcaccagtgaacaagcggttgatgaat
agccatatgacaggatcgtcaaaactcttcctgatgactgaacgaaaatt
ctggttagaccatatcctcccgtcttgtgtcctcatggacgggatcgcaa
aagcagtgtattgcctggactatgagtcgcaggatccgaatggtaaaggt
ctagtgctcatcagttatacatgggaggacgactcccacaagctgttggc
ggtccccgacaaaaagagcgattatgtctgctgcgggacgcaatttcga
gatctttcccggcgtttgcccagcacctattttcctgcctgcgctgattac
gaccaaaatgttattcaactgattggcttacagacgagaatgccggggcg
agctttcaaactcaaccggcgtggtgaggattttttattctgaagaacttt
tctttcaagcactggacacggctaataccggagtttacttggcgggt
tgcagttgttccttcacaggtggatgggtggagggtgctattcagaccgc Appendix-continued gtgtaacgccgtctgtgcaattatccacaattgtggaggcattttggcaa
agggcaatcctctcgaacactcttggaagagataaactaccgcactaga
aattag SbUGT::CKX (nt) (SEQ ID NO: 7)

*ctagaagaccagataaacgatacgtaagcaagtacgtcatcaaataagct*
*tctcctctctctgtttctataattatatattagtcgagacttcattgagc*
*aaaatcctatattgcatccttctcatgcaggccaccataaatattccat*
*tccaagaattccaaatttgcaaatatacacataattaaa*atggctaatctt
cgtttaatgatcacttaatcacggttaatgatcaccaaatcatcaaa
cggtattaaaattgatttacctaaatcccttaacctcaccctctctaccg
atccttccatcatctccgcagcctctcatgacttcggaaacataaccacc
gtgacccccggcggcgtaatctgccctcctccaccgctgatatctctcg
tctcctccaatacgccgcaaacgggaaaagtacattccaagtagcggctc
gtggccaaggccactccttaaacggccaagcctcggtctccggcggagta
atcgtcaacatgacgtgtatcactgacgtggtggtttcaaaagacaagaa
gtacgctgacgtggcggccagggacgttatgggtggatgtgcttaagaaga
cggcggagaaaggggtgtcgccggtttcttggacggattatttgcatata
accgtcggaggaacgttgtcgaatggtgaattggtggtcaagtgtttcg
aaacggtcctcttgttagtaacgtccttgaattggacgttattactggga
aaggtgaaatgttgacatgctcgcgacagctaaacccagaagttgttctat
ggagtgttaggaggtttgggtcaatttggaattataacgagagccagaat
tgtttttggaccatgcacctaaacgggccaaatggttcggatgctctaca
gtgatttcacaacttttacaaaggaccaagaacgtttgatatcaatggca
aacgatattggagtcgactatttagaaggtcaaatatttctatcaaacgg
tgtcgttgacaccctctttttttcccaccttcagatcaatctaaagtcgctg
atctagtcaagcaacacggtatcatctatgttcttgaagtagccaagtat
tatgatgatcccaatctccccatcatcagcaaggttattgacacattaac
gaaaacattaagttacttgcccggttcatatcaatgcacgacgtggcct
acttcgatttcttgaaccgtgtacatgtcgaagaaaataaactcagatct
ttgggattatgggaacttcctcatccttggcttaacctctacgttcctaa
atctcggattctcgattttcataacggtgttgtcaaagacattcttctta
agcaaaaatcagcttcgggactcgctcttctctatccaacaaaccggaat
aaatgggacaatcgtatgtcggcgatgatcaccagagatcgatgaagatgt
tatatatattatcggactactacaatccgctaccccaaaggatcttccag
aagtggagagcgttaacgagaagataattaggttttgcaaggattcaggt
attaagattaagcaatatctaatgcattatactagtaaagaagattggat
tgagcattttggatcaaaatgggatgattttttcgaagaggaaagatctat
ttgatcccaagaaactgttatctccagggcaagacatctttttga

What is claimed is:

1. A transgenic rootstock plant comprising:
   an auxin synthesis-related iaaM coding sequence consisting the polynucleotide sequence of SEQ ID NO: 2 that encodes the polypeptide sequence of SEQ ID NO: 3, and wherein the auxin synthesis-related iaaM coding sequence is operably linked to a SbUGT promoter consisting the polynucleotide sequence of SEQ ID NO: 1;
   a cytokinin degradation-related CKX coding sequence consisting the polynucleotide sequence of SEQ ID NO: 4 that encodes the polypeptide sequence of SEQ ID NO: 5, and wherein the cytokinin degradation-related CKX coding sequence is operably linked to a SbUGT promoter consisting the polynucleotide sequence of SEQ ID NO: 1; and
   wherein overexpression of the polypeptides of SEQ ID NO: 3 and SEQ ID NO: 4 in the transgenic rootstock plant results in enhanced root initiation, enhanced root biomass, inhibited lateral bud release from the transgenic rootstock, and improved grafting success rates as compared to control or wild-type plants of the same species grown under identical conditions.

2. A method of producing a transgenic rootstock plant, the method comprising:
   (a) transforming a plant cell with a DNA construct comprising (i) an auxin synthesis-related iaaM coding sequence consisting the polynucleotide sequence of SEQ ID NO: 2 that encodes the polypeptide sequence of SEQ ID NO: 3, and wherein the auxin synthesis-related iaaM coding sequence is operably linked to a SbUGT promoter consisting the polynucleotide sequence of SEQ ID NO: 1, and (ii) a cytokinin degradation-related CKX coding sequence consisting the polynucleotide sequence of SEQ ID NO: 4 that encodes the polypeptide of SEQ ID NO: 5, and wherein the cytokinin degradation-related CKX coding sequence is operably linked to a SbUGT promoter consisting the polynucleotide sequence of SEQ ID NO: 1; and
   (b) regenerating the transformed plant cell to produce a transgenic rootstock plant;
   wherein overexpression of the polypeptides of SEQ ID NO: 3 and SEQ ID NO: 4 in the transgenic rootstock plant results in enhanced root initiation, enhanced root biomass, inhibited lateral bud release from the transgenic rootstock, and improved grafting success rates as compared to control or wild-type plants of the same species grown under identical conditions.

3. A method of producing a transgenic rootstock plant, the method comprising:
   (a) obtaining a first transgenic plant comprising an auxin synthesis-related iaaM coding sequence consisting the polynucleotide sequence of SEQ ID NO: 2 that encodes the polypeptide sequence SEQ ID NO: 3, and wherein the auxin synthesis-related iaaM coding sequence is operably linked to a SbUGT promoter consisting the polynucleotide sequence of SEQ ID NO: 1;
   (b) obtaining a second transgenic plant comprising a cytokinin degradation-related CKX coding sequence consisting the polynucleotide sequence of SEQ ID NO: 4 that encodes the polypeptide of SEQ ID NO: 5, and wherein the cytokinin degradation-related CKX coding sequence is operably linked to a SbUGT promoter consisting the polynucleotide sequence of SEQ ID NO: 1; and
   (c) generating a cross between the first transgenic plant and the second transgenic plant to produce the transgenic rootstock plant;
   wherein overexpression of the polypeptides of SEQ ID NO: 3 and SEQ ID NO: 4 in the transgenic rootstock plant results in enhanced root initiation, enhanced root biomass, inhibited lateral bud release from the transgenic rootstock, and improved grafting success rates as compared to control or wild-type plants of the same species grown under identical conditions.

4. A transgenic rootstock plant produced by the method of claim 2.

5. The transgenic rootstock plant of claim 1, wherein the transgenic rootstock plant is a fruit tree, a nut tree, a woody shrub, a hardwood tree, a softwood tree, a crop plant, a legume, a vegetable, a root crop, a non-food crop, or an ornamental plant.

6. The transgenic rootstock plant of claim 1, wherein the transgenic rootstock plant is a tree.

7. A method of producing a grafted plant, the method comprising contacting the transgenic rootstock plant of claim 4 with a scion.

8. The transgenic rootstock plant of claim 2, wherein the transgenic rootstock plant is a fruit tree, a nut tree, a woody shrub, a hardwood tree, a softwood tree, a crop plant, a legume, a vegetable, a root crop, a non-food crop, or an ornamental plant.

9. The transgenic rootstock plant of claim 2, wherein the transgenic rootstock plant is a tree.

10. A transgenic rootstock plant produced by the method of claim 3.

11. The transgenic rootstock plant of claim 3, wherein the transgenic rootstock plant is a fruit tree, a nut tree, a woody shrub, a hardwood tree, a softwood tree, a crop plant, a legume, a vegetable, a root crop, a non-food crop, or an ornamental plant.

12. The transgenic rootstock plant of claim 3, wherein the transgenic rootstock plant is a tree.

* * * * *

SEQUENCE LISTING

<160> NUMBER OF SEQ ID NOS: 17

<210> SEQ ID NO 1
<211> LENGTH: 188
<212> TYPE: DNA
<213> ORGANISM: Artificial sequence
<220> FEATURE:
<223> OTHER INFORMATION: Synthetic

<400> SEQUENCE: 1
ctagaagacc agataaacga tacgtaagca agtacgtcat caaataagct tctcctctct    60
ctgtttctat aattatatat tagtcgagac ttcattgagc aaaatcctat attgcatcct   120
ttctcatgca ggccaccata atattccat tccaagaatt ccaaatttgc aaatatacac   180
ataattaa                                                           188

<210> SEQ ID NO 2
<211> LENGTH: 2268
<212> TYPE: DNA
<213> ORGANISM: Agrobacterium tumefaciens

<400> SEQUENCE: 2
atgtcagctt cacctctcct tgataaccag tgcgatcatc tcccaaccaa aatggtggat    60
ctgacaatgg tcgataaggc ggatgaattg gaccgcaggg tttccgatgc cttcttagaa   120
cgagaagctt ctagggaag gaggattact caaatctcca ccgagtgcag cgctgggtta   180
gcttgcaaaa ggctggccga tggtcgcttc cccgagatct cagctggtgg aaaggtagca   240

```
gttctctccg cttatatcta tattggcaaa gaaattctgg ggcggatact tgaatcgaaa      300
ccttgggcgc gggcaacagt gagtggtctc gttgccatcg acttggcacc attttgcatg      360
gatttctccg aagcacaact aatccaagcc ctgttttgc tgagcggtaa agatgtgca        420 ccgattgatc ttagtcattt cgtggccatt tcaatctcta agactgccgg ctttcgaacc      480
ctgccaatgc cgctgtacga gaatggcacg atgaaatgcg ttaccgggtt taccataacc     540
cttgaagggg ccgtgccatt tgacatggta gcttatggtc gaaacctgat gctgaagggt     600
tcggcaggtt cctttccaac aatcgacttg ctctacgact acagaccgtt ttttgaccaa     660
tgttccgata gtggacggat cggcttcttt ccggaggatg ttcctaagcc gaaagtggcg     720
gtcattggcg ctggcatttc cggactcgtg gtggcaaacg aactgcttca tgctggggta     780
gacgatgtta caatatatga agcaagtgat cgtgttggag gcaagctttg gtcacatgct     840
ttcagggacg ctcctagtgt cgtggccgaa atgggggcga tgcgatttcc tcctgctgca     900
ttctgcttgt ttttcttcct cgagcgttac ggcctgtctt cgatgaggcc gttcccaaat     960
cccggcacag tcgacactta cttggtctac caaggcgtcc aatacatgtg aaagccggg     1020 cagctgccac cgaagctgtt ccatcgcgtt tacaacggtt ggcgtgcgtt cttgaaggac    1080
ggttttcatg agcgagatat tgtgttggct tcgcctgtcg ctattactca ggccttgaaa    1140
tcaggagaca ttaggtgggc tcatgactcc tggcaaattt ggctgaaccg tttcgggagg    1200
gagtccttct cttcagggat agagaggatc tttctgggca cacatcctcc tggtggtgaa    1260
acatggagtt ttcctcatga ttgggaccta ttcaagctaa tgggaatagg atctggcggg    1320
tttggtccag tttttgaaag cgggtttatt gagatcctcc gcttggtcat caacggatat    1380
gaagaaaatc agcggatgtg ccctgaagga atctcagaac ttccacgtcg gatcgcatct    1440
gaagtggtta acggtgtgtc tgtgagccag cgcatatgcc atgttcaagt cagggcgatt    1500
cagaaggaaa agacaaaaat aaagataagg cttaagagcg ggatatctga actttatgat    1560
aaggtggtgg tcacatctgg actcgcaaat atccaactca ggcattgcct gacatgcgat    1620
accaatattt ttcaggcacc agtgaaccaa gcggttgata acagccatat gacaggatcg    1680
tcaaaactct tcctgatgac tgaacgaaaa ttctggttag accatatcct cccgtcttgt    1740
gtcctcatgg acgggatcgc aaaagcagtg tattgcctgg actatgagtc gcaggatccg    1800
aatggtaaag gtctagtgct catcagttat acatgggagg acgactccca caagctgttg    1860
gcggtccccg acaaaaaaga gcgattatgt ctgctgcggg acgcaatttc gagatctttc    1920
ccggcgtttg cccagcacct atttcctgcc tgcgctgatt acgaccaaaa tgttattcaa    1980
catgattggc ttacagacga gaatgccggg ggagctttca aactcaaccg gcgtggtgag    2040
gatttttatt ctgaagaact tttctttcaa gcactggaca cggctaatga taccggagtt    2100
tacttggcgg gttgcagttg ttccttcaca ggtggatggg tggagggtgc tattcagacc    2160
gcgtgtaacg ccgtctgtgc aattatccac aattgtggag cattttggc aaagggcaat    2220 cctctcgaac actcttggaa gagatataac taccgcacta gaaattag                 2268
```

<210> SEQ ID NO 3
<211> LENGTH: 755
<212> TYPE: PRT
<213> ORGANISM: Agrobacterium tumefaciens

<400> SEQUENCE: 3

Met Ser Ala Ser Pro Leu Leu Asp Asn Gln Cys Asp His Leu Pro Thr
1               5                   10                  15

```
Lys Met Val Asp Leu Thr Met Val Asp Lys Ala Asp Glu Leu Asp Arg
            20                  25                  30

Arg Val Ser Asp Ala Phe Leu Glu Arg Glu Ala Ser Arg Gly Arg Arg
        35                  40                  45

Ile Thr Gln Ile Ser Thr Glu Cys Ser Ala Gly Leu Ala Cys Lys Arg
    50                  55                  60

Leu Ala Asp Gly Arg Phe Pro Glu Ile Ser Ala Gly Lys Val Ala
65                  70                  75                  80

Val Leu Ser Ala Tyr Ile Tyr Ile Gly Lys Glu Ile Leu Gly Arg Ile
                85                  90                  95

Leu Glu Ser Lys Pro Trp Ala Arg Ala Thr Val Ser Gly Leu Val Ala
            100                 105                 110

Ile Asp Leu Ala Pro Phe Cys Met Asp Phe Ser Glu Ala Gln Leu Ile
        115                 120                 125

Gln Ala Leu Phe Leu Leu Ser Gly Lys Arg Cys Ala Pro Ile Asp Leu
130                 135                 140

Ser His Phe Val Ala Ile Ser Ile Ser Lys Thr Ala Gly Phe Arg Thr
145                 150                 155                 160

Leu Pro Met Pro Leu Tyr Glu Asn Gly Thr Met Lys Cys Val Thr Gly
                165                 170                 175

Phe Thr Ile Thr Leu Glu Gly Ala Val Pro Phe Asp Met Val Ala Tyr
            180                 185                 190

Gly Arg Asn Leu Met Leu Lys Gly Ser Ala Gly Ser Phe Pro Thr Ile
        195                 200                 205

Asp Leu Leu Tyr Asp Tyr Arg Pro Phe Phe Asp Gln Cys Ser Asp Ser
    210                 215                 220

Gly Arg Ile Gly Phe Phe Pro Glu Asp Val Pro Lys Pro Lys Val Ala
225                 230                 235                 240

Val Ile Gly Ala Gly Ile Ser Gly Leu Val Val Ala Asn Glu Leu Leu
                245                 250                 255

His Ala Gly Val Asp Asp Val Thr Ile Tyr Glu Ala Ser Asp Arg Val
            260                 265                 270

Gly Gly Lys Leu Trp Ser His Ala Phe Arg Asp Ala Pro Ser Val Val
        275                 280                 285

Ala Glu Met Gly Ala Met Arg Phe Pro Pro Ala Ala Phe Cys Leu Phe
    290                 295                 300

Phe Phe Leu Glu Arg Tyr Gly Leu Ser Ser Met Arg Pro Phe Pro Asn
305                 310                 315                 320

Pro Gly Thr Val Asp Thr Tyr Leu Val Tyr Gln Gly Val Gln Tyr Met
                325                 330                 335

Trp Lys Ala Gly Gln Leu Pro Pro Lys Leu Phe His Arg Val Tyr Asn
            340                 345                 350

Gly Trp Arg Ala Phe Leu Lys Asp Gly Phe His Glu Arg Asp Ile Val
        355                 360                 365

Leu Ala Ser Pro Val Ala Ile Thr Gln Ala Leu Lys Ser Gly Asp Ile
    370                 375                 380

Arg Trp Ala His Asp Ser Trp Gln Ile Trp Leu Asn Arg Phe Gly Arg
385                 390                 395                 400

Glu Ser Phe Ser Ser Gly Ile Glu Arg Ile Phe Leu Gly Thr His Pro
                405                 410                 415

Pro Gly Gly Glu Thr Trp Ser Phe Pro His Asp Trp Asp Leu Phe Lys
            420                 425                 430
```

Leu Met Gly Ile Gly Ser Gly Gly Phe Gly Pro Val Phe Glu Ser Gly
            435                 440                 445

Phe Ile Glu Ile Leu Arg Leu Val Ile Asn Gly Tyr Glu Glu Asn Gln
450                 455                 460

Arg Met Cys Pro Glu Gly Ile Ser Glu Leu Pro Arg Arg Ile Ala Ser
465                 470                 475                 480

Glu Val Val Asn Gly Val Ser Val Ser Gln Arg Ile Cys His Val Gln
                485                 490                 495

Val Arg Ala Ile Gln Lys Glu Lys Thr Lys Ile Lys Ile Arg Leu Lys
            500                 505                 510

Ser Gly Ile Ser Glu Leu Tyr Asp Lys Val Val Thr Ser Gly Leu
            515                 520                 525

Ala Asn Ile Gln Leu Arg His Cys Leu Thr Cys Asp Thr Asn Ile Phe
530                 535                 540

Gln Ala Pro Val Asn Gln Ala Val Asp Asn Ser His Met Thr Gly Ser
545                 550                 555                 560

Ser Lys Leu Phe Leu Met Thr Glu Arg Lys Phe Trp Leu Asp His Ile
                565                 570                 575

Leu Pro Ser Cys Val Leu Met Asp Gly Ile Ala Lys Ala Val Tyr Cys
            580                 585                 590

Leu Asp Tyr Glu Ser Gln Asp Pro Asn Gly Lys Gly Leu Val Leu Ile
            595                 600                 605

Ser Tyr Thr Trp Glu Asp Ser His Lys Leu Leu Ala Val Pro Asp
            610                 615                 620

Lys Lys Glu Arg Leu Cys Leu Leu Arg Asp Ala Ile Ser Arg Ser Phe
625                 630                 635                 640

Pro Ala Phe Ala Gln His Leu Phe Pro Ala Cys Ala Asp Tyr Asp Gln
                645                 650                 655

Asn Val Ile Gln His Asp Trp Leu Thr Asp Glu Asn Ala Gly Gly Ala
            660                 665                 670

Phe Lys Leu Asn Arg Arg Gly Glu Asp Phe Tyr Ser Glu Glu Leu Phe
            675                 680                 685

Phe Gln Ala Leu Asp Thr Ala Asn Asp Thr Gly Val Tyr Leu Ala Gly
690                 695                 700

Cys Ser Cys Ser Phe Thr Gly Trp Val Glu Gly Ala Ile Gln Thr
705                 710                 715                 720

Ala Cys Asn Ala Val Cys Ala Ile Ile His Asn Cys Gly Gly Ile Leu
                725                 730                 735

Ala Lys Gly Asn Pro Leu Glu His Ser Trp Lys Arg Tyr Asn Tyr Arg
            740                 745                 750

Thr Arg Asn
        755

<210> SEQ ID NO 4
<211> LENGTH: 1506
<212> TYPE: DNA
<213> ORGANISM: Arabidopsis thaliana

<400> SEQUENCE: 4
atggctaatc ttcgtttaat gatcacttta atcacggttt taatgatcac caaatcatca      60
aacggtatta aaattgattt acctaaatcc cttaacctca ccctctctac cgatccttcc     120
atcatctccg cagcctctca tgacttcgga aacataacca ccgtgacccc cggcggcgta     180
atctgcccct cctccaccgc tgatatctct cgtctcctcc aatacgccgc aaacggaaaa     240

```
agtacattcc aagtagcggc tcgtggccaa ggccactcct taaacggcca agcctcggtc    300
tccggcggag taatcgtcaa catgacgtgt atcactgacg tggtggtttc aaaagacaag    360
aagtacgctg acgtggcggc cgggacgtta tgggtggatg tgcttaagaa gacggcggag    420 aaagggtgt cgccggtttc ttggacggat tatttgcata taaccgtcgg aggaacgttg    480
tcgaatggtg gaattggtgg tcaagtgttt cgaaacggtc ctcttgttag taacgtcctt    540
gaattggacg ttattactgg gaaaggtgaa atgttgacat gctcgcgaca gctaaaccca    600
gaattgttct atggagtgtt aggaggtttg ggtcaatttg gaattataac gagagccaga    660
attgttttgg accatgcacc taaacgggcc aaatggtttc ggatgctcta cagtgatttc    720 acaacttta caaggacca agaacgtttg atatcaatgg caaacgatat tggagtcgac    780
tatttagaag gtcaaatatt tctatcaaac ggtgtcgttg acacctcttt tttcccacct    840
tcagatcaat ctaaagtcgc tgatctagtc aagcaacacg gtatcatcta tgttcttgaa    900
gtagccaagt attatgatga tcccaatctc cccatcatca gcaaggttat tgacacatta    960
acgaaaacat taagttactt gcccgggttc atatcaatgc acgacgtggc ctacttcgat   1020
ttcttgaacc gtgtacatgt cgaagaaaat aaactcagat ctttgggatt atgggaactt   1080
cctcatcctt ggcttaacct ctacgttcct aaatctcgga ttctcgattt tcataacggt   1140
gttgtcaaag acattcttct taagcaaaaa tcagcttcgg gactcgctct tctctatcca   1200
acaaaccgga taaatggga caatcgtatg tcggcgatga taccagagat cgatgaagat   1260
gttatatata ttatcggact actacaatcc gctaccccaa aggatcttcc agaagtggag   1320
agcgttaacg agaagataat taggttttgc aaggattcag gtattaagat taagcaatat   1380
ctaatgcatt atactagtaa agaagattgg attgagcatt ttggatcaaa atgggatgat   1440
ttttcgaaga ggaaagatct atttgatccc aagaaactgt tatctccagg gcaagacatc   1500
ttttga                                                                1506
```

<210> SEQ ID NO 5
<211> LENGTH: 501
<212> TYPE: PRT
<213> ORGANISM: Arabidopsis thaliana

<400> SEQUENCE: 5

```
Met Ala Asn Leu Arg Leu Met Ile Thr Leu Ile Thr Val Leu Met Ile
1               5                   10                  15

Thr Lys Ser Ser Asn Gly Ile Lys Ile Asp Leu Pro Lys Ser Leu Asn
                20                  25                  30

Leu Thr Leu Ser Thr Asp Pro Ser Ile Ile Ser Ala Ala Ser His Asp
            35                  40                  45

Phe Gly Asn Ile Thr Thr Val Thr Pro Gly Gly Val Ile Cys Pro Ser
        50                  55                  60

Ser Thr Ala Asp Ile Ser Arg Leu Leu Gln Tyr Ala Ala Asn Gly Lys
65                  70                  75                  80

Ser Thr Phe Gln Val Ala Ala Arg Gly Gln Gly His Ser Leu Asn Gly
                85                  90                  95

Gln Ala Ser Val Ser Gly Gly Val Ile Val Asn Met Thr Cys Ile Thr
            100                 105                 110

Asp Val Val Ser Lys Asp Lys Lys Tyr Ala Asp Val Ala Ala Gly
        115                 120                 125

Thr Leu Trp Val Asp Val Leu Lys Lys Thr Ala Glu Lys Gly Val Ser
    130                 135                 140
```

```
Pro Val Ser Trp Thr Asp Tyr Leu His Ile Thr Val Gly Gly Thr Leu
145                 150                 155                 160

Ser Asn Gly Gly Ile Gly Gly Gln Val Phe Arg Asn Gly Pro Leu Val
            165                 170                 175

Ser Asn Val Leu Glu Leu Asp Val Ile Thr Gly Lys Gly Glu Met Leu
        180                 185                 190

Thr Cys Ser Arg Gln Leu Asn Pro Glu Leu Phe Tyr Gly Val Leu Gly
    195                 200                 205

Gly Leu Gly Gln Phe Gly Ile Ile Thr Arg Ala Arg Ile Val Leu Asp
    210                 215                 220

His Ala Pro Lys Arg Ala Lys Trp Phe Arg Met Leu Tyr Ser Asp Phe
225                 230                 235                 240

Thr Thr Phe Thr Lys Asp Gln Glu Arg Leu Ile Ser Met Ala Asn Asp
                245                 250                 255

Ile Gly Val Asp Tyr Leu Glu Gly Gln Ile Phe Leu Ser Asn Gly Val
            260                 265                 270

Val Asp Thr Ser Phe Phe Pro Pro Ser Asp Gln Ser Lys Val Ala Asp
        275                 280                 285

Leu Val Lys Gln His Gly Ile Ile Tyr Val Leu Glu Val Ala Lys Tyr
    290                 295                 300

Tyr Asp Asp Pro Asn Leu Pro Ile Ile Ser Lys Val Ile Asp Thr Leu
305                 310                 315                 320

Thr Lys Thr Leu Ser Tyr Leu Pro Gly Phe Ile Ser Met His Asp Val
                325                 330                 335

Ala Tyr Phe Asp Phe Leu Asn Arg Val His Val Glu Glu Asn Lys Leu
            340                 345                 350

Arg Ser Leu Gly Leu Trp Glu Leu Pro His Pro Trp Leu Asn Leu Tyr
        355                 360                 365

Val Pro Lys Ser Arg Ile Leu Asp Phe His Asn Gly Val Val Lys Asp
    370                 375                 380

Ile Leu Leu Lys Gln Lys Ser Ala Ser Gly Leu Ala Leu Leu Tyr Pro
385                 390                 395                 400

Thr Asn Arg Asn Lys Trp Asp Asn Arg Met Ser Ala Met Ile Pro Glu
                405                 410                 415

Ile Asp Glu Asp Val Ile Tyr Ile Ile Gly Leu Leu Gln Ser Ala Thr
            420                 425                 430

Pro Lys Asp Leu Pro Glu Val Glu Ser Val Asn Glu Lys Ile Ile Arg
        435                 440                 445

Phe Cys Lys Asp Ser Gly Ile Lys Ile Lys Gln Tyr Leu Met His Tyr
    450                 455                 460

Thr Ser Lys Glu Asp Trp Ile Glu His Phe Gly Ser Lys Trp Asp Asp
465                 470                 475                 480

Phe Ser Lys Arg Lys Asp Leu Phe Asp Pro Lys Lys Leu Leu Ser Pro
                485                 490                 495

Gly Gln Asp Ile Phe
            500
```

<210> SEQ ID NO 6
<211> LENGTH: 2456
<212> TYPE: DNA
<213> ORGANISM: Artificial sequence
<220> FEATURE:
<223> OTHER INFORMATION: Synthetic

<400> SEQUENCE: 6

```
ctagaagacc agataaacga tacgtaagca agtacgtcat caaataagct tctcctctct    60
ctgtttctat aattatatat tagtcgagac ttcattgagc aaaatcctat attgcatcct   120
ttctcatgca ggccaccata aatattccat tccaagaatt ccaaatttgc aaatatacac   180
ataattaaat gtcagcttca cctctccttg ataaccagtg cgatcatctc caaccaaaa    240 tggtggatct gacaatggtc gataaggcgg atgaattgga ccgcagggtt tccgatgcct   300
tcttagaacg agaagcttct aggggaagga ggattactca aatctccacc gagtgcagcg   360
ctgggttagc ttgcaaaagg ctggccgatg gtcgcttccc cgagatctca gctggtggaa   420
aggtagcagt tctctccgct tatatctata ttggcaaaga aattctgggg cggatacttg   480
aatcgaaacc ttgggcgcgg gcaacagtga gtggtctcgt tgccatcgac ttggcaccat   540
tttgcatgga tttctccgaa gcacaactaa tccaagccct gttttgctg agcggtaaaa    600 gatgtgcacc gattgatctt agtcatttcg tggccatttc aatctctaag actgccggct   660
ttcgaaccct gccaatgccg ctgtacgaga atggcacgat gaaatgcgtt accgggttta   720
ccataaccct tgaaggggcc gtgccatttg acatggtagc ttatggtcga aacctgatgc   780
tgaagggttc ggcaggttcc tttccaacaa tcgacttgct ctacgactac agaccgtttt   840
ttgaccaatg ttccgatagt ggacggatcg gcttctttcc ggaggatgtt cctaagccga   900
aagtggcggt cattggcgct ggcatttccg gactcgtggt ggcaaacgaa ctgcttcatg   960
ctggggtaga cgatgttaca atatatgaag caagtgatcg tgttggaggc aagctttggt  1020
cacatgcttt cagggacgct cctagtgtcg tggccgaaat gggggcgatg cgatttcctc  1080
ctgctgcatt ctgcttgttt ttcttcctcg agcgttacgg cctgtcttcg atgaggccgt  1140
tcccaaatcc cggcacagtc gacacttact tggtctacca aggcgtccaa tacatgtgga  1200
aagccgggca gctgccaccg aagctgttcc atcgcgttta caacggttgg cgtgcgttct  1260
tgaaggacgg ttttcatgag cgagatattg tgttggcttc gcctgtcgct attactcagg  1320
ccttgaaatc aggagacatt aggtgggctc atgactcctg gcaaatttgg ctgaaccgtt  1380
tcgggaggga gtccttctct tcagggatag agaggatctt tctgggcaca catcctcctg  1440
gtggtgaaac atggagtttt cctcatgatt gggacctatt caagctaatg gaataggat    1500 ctggcgggtt tggtccagtt tttgaaagcg ggtttattga gatcctccgc ttggtcatca  1560
acggatatga agaaaatcag cggatgtgcc ctgaaggaat ctcagaactt ccacgtcgga  1620
tcgcatctga agtggttaac ggtgtgtctg tgagccagcg catatgccat gttcaagtca  1680
gggcgattca gaaggaaaag acaaaaataa agataaggct taagagcggg atatctgaac  1740
tttatgataa ggtggtggtc acatctggac tcgcaaatat ccaactcagg cattgcctga  1800
catgcgatac caatattttt caggcaccag tgaaccaagc ggttgataac agccatatga  1860
caggatcgtc aaaactcttc ctgatgactg aacgaaaatt ctggttagac catatcctcc  1920
cgtcttgtgt cctcatggac gggatcgcaa aagcagtgta ttgcctggac tatgagtcgc  1980
aggatccgaa tggtaaaggt ctagtgctca tcagttatac atgggaggac gactcccaca  2040
agctgttggc ggtccccgac aaaaaagagc gattatgtct gctgcgggac gcaatttcga  2100
gatctttccc ggcgtttgcc cagcacctat tcctgcctg cgctgattac gaccaaaatg   2160
ttattcaaca tgattggctt acagacgaga atgccggggg agctttcaaa ctcaaccggc  2220
gtggtgagga ttttattcct gaagaacttt tctttcaagc actggacacg gctaatgata  2280
ccggagttta cttggcgggt tgcagttgtt ccttcacagg tggatgggtg gagggtgcta  2340
ttcagaccgc gtgtaacgcc gtctgtgcaa ttatccacaa ttgtggaggc attttggcaa  2400
```
agggcaatcc tctcgaacac tcttggaaga gatataacta ccgcactaga aattag      2456

<210> SEQ ID NO 7
<211> LENGTH: 1694
<212> TYPE: DNA
<213> ORGANISM: Artificial sequence
<220> FEATURE:
<223> OTHER INFORMATION: Synthetic

<400> SEQUENCE: 7
ctagaagacc agataaacga tacgtaagca agtacgtcat caaataagct tctcctctct      60
ctgtttctat aattatatat tagtcgagac ttcattgagc aaaatcctat attgcatcct     120
ttctcatgca ggccaccata aatattccat tccaagaatt ccaaatttgc aaatatacac     180
ataattaaat ggctaatctt cgtttaatga tcactttaat cacggtttta atgatcacca     240
aatcatcaaa cggtattaaa attgatttac ctaaatccct taacctcacc ctctctaccg     300
atccttccat catctccgca gcctctcatg acttcggaaa cataaccacc gtgacccccg     360
gcggcgtaat ctgcccctcc tccaccgctg atatctctcg tctcctccaa tacgccgcaa     420
acggaaaaag tacattccaa gtagcggctc gtggccaagg ccactcctta aacgccaag      480
cctcggtctc cggcggagta atcgtcaaca tgacgtgtat cactgacgtg gtggtttcaa     540
aagacaagaa gtacgctgac gtggcggccg ggacgttatg ggtggatgtg cttaagaaga     600
cggcggagaa aggggtgtcg ccggtttctt ggacggatta tttgcatata accgtcggag     660
gaacgttgtc gaatggtgga attggtggtc aagtgtttcg aaacggtcct cttgttagta     720
acgtccttga attggacgtt attactggga aaggtgaaat gttgacatgc tcgcgacagc     780
taaacccaga attgttctat ggagtgttag gaggtttggg tcaatttgga attataacga     840
gagccagaat tgttttggac catgcaccta acgggccaa atggtttcgg atgctctaca      900
gtgatttcac aacttttaca aaggaccaag aacgttgat atcaatggca acgatattg        960
gagtcgacta tttagaaggt caaatatttc tatcaaacgg tgtcgttgac acctcttttt    1020
tcccaccttc agatcaatct aaagtcgctg atctagtcaa gcaacacggt atcatctatg    1080
ttcttgaagt agccaagtat tatgatgatc ccaatctccc catcatcagc aaggttattg    1140
acacattaac gaaaacatta agttacttgc ccggggttcat atcaatgcac gacgtggcct    1200
acttcgattt cttgaaccgt gtacatgtcg aagaaaataa actcagatct ttgggattat    1260
gggaacttcc tcatccttgg cttaacctct acgttcctaa atctcggatt ctcgattttc    1320
ataacggtgt tgtcaaagac attcttctta agcaaaaatc agcttcggga ctcgctcttc    1380
tctatccaac aaaccggaat aaatgggaca tcgtatgtc ggcgatgata ccagagatcg      1440
atgaagatgt tatatatatt atcggactac taatccgc tacccaaag gatcttccag         1500
aagtggagag cgttaacgag aagataatta ggttttgcaa ggattcaggt attaagatta    1560
agcaatatct aatgcattat actagtaaag aagattggat tgagcatttt ggatcaaaat    1620
gggatgattt ttcgaagagg aaagatctat ttgatcccaa gaaactgtta tctccagggc    1680
aagacatctt ttga                                                      1694

<210> SEQ ID NO 8
<211> LENGTH: 18
<212> TYPE: DNA
<213> ORGANISM: Artificial sequence
<220> FEATURE:
<223> OTHER INFORMATION: Sythetic

<400> SEQUENCE: 8
ttctccgaag cacaacta                                                        18

<210> SEQ ID NO 9
<211> LENGTH: 17
<212> TYPE: DNA
<213> ORGANISM: Artificial sequence
<220> FEATURE:
<223> OTHER INFORMATION: Sythetic

<400> SEQUENCE: 9
gcccacctaa tgtctcc                                                         17

<210> SEQ ID NO 10
<211> LENGTH: 17
<212> TYPE: DNA
<213> ORGANISM: Artificial sequence
<220> FEATURE:
<223> OTHER INFORMATION: Synthetic

<400> SEQUENCE: 10
cgttatgggt ggatgtg                                                         17

<210> SEQ ID NO 11
<211> LENGTH: 17
<212> TYPE: DNA
<213> ORGANISM: Artificial sequence
<220> FEATURE:
<223> OTHER INFORMATION: Synthetic

<400> SEQUENCE: 11
taagccaagg atgagga                                                         17

<210> SEQ ID NO 12
<211> LENGTH: 19
<212> TYPE: DNA
<213> ORGANISM: Artificial sequence
<220> FEATURE:
<223> OTHER INFORMATION: Synthetic

<400> SEQUENCE: 12
tggatttctc cgaagcaca                                                       19

<210> SEQ ID NO 13
<211> LENGTH: 18
<212> TYPE: DNA
<213> ORGANISM: Artificial sequence
<220> FEATURE:
<223> OTHER INFORMATION: Synthetic

<400> SEQUENCE: 13
cccggtaacg catttcat                                                        18

<210> SEQ ID NO 14
<211> LENGTH: 19
<212> TYPE: DNA
<213> ORGANISM: Artificial sequence
<220> FEATURE:
<223> OTHER INFORMATION: Synthetic

<400> SEQUENCE: 14
ggattatgca atttcaagg                                                       19

<210> SEQ ID NO 15
<211> LENGTH: 19

```
<212> TYPE: DNA
<213> ORGANISM: Artificial sequence
<220> FEATURE:
<223> OTHER INFORMATION: Synthetic

<400> SEQUENCE: 15
acgatgggct aaagtgtct                                              19

<210> SEQ ID NO 16
<211> LENGTH: 20
<212> TYPE: DNA
<213> ORGANISM: Artificial sequence
<220> FEATURE:
<223> OTHER INFORMATION: Synthetic

<400> SEQUENCE: 16
gctgctcaga agaagaaatg                                             20

<210> SEQ ID NO 17
<211> LENGTH: 21
<212> TYPE: DNA
<213> ORGANISM: Artificial sequence
<220> FEATURE:
<223> OTHER INFORMATION: Synthetic

<400> SEQUENCE: 17
gagctggttc cagacataca c                                           21
```